(12) United States Patent
Davis et al.

(10) Patent No.: US 9,108,979 B2
(45) Date of Patent: Aug. 18, 2015

(54) DIELS-ALDER REACTIONS CATALYZED BY LEWIS ACID CONTAINING SOLIDS: RENEWABLE PRODUCTION OF BIO-PLASTICS

(71) Applicant: CALIFORNIA INSTITUTE OF TECHNOLOGY, Pasadena, CA (US)

(72) Inventors: Mark E. Davis, Pasadena, CA (US); Joshua Pacheco, North Hollywood, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/282,099

(22) Filed: May 20, 2014

(65) Prior Publication Data

US 2014/0364631 A1    Dec. 11, 2014

Related U.S. Application Data

(60) Provisional application No. 61/936,213, filed on Feb. 5, 2014, provisional application No. 61/909,131, filed on Nov. 26, 2013, provisional application No. 61/831,999, filed on Jun. 6, 2013.

(51) Int. Cl.
| | |
|---|---|
| *C07C 51/353* | (2006.01) |
| *C07D 493/08* | (2006.01) |
| *C07C 2/86* | (2006.01) |
| *C07C 29/32* | (2006.01) |
| *C07C 67/343* | (2006.01) |
| *C07C 45/70* | (2006.01) |

(52) U.S. Cl.
CPC .............. *C07D 493/08* (2013.01); *C07C 2/862* (2013.01); *C07C 29/32* (2013.01); *C07C 45/70* (2013.01); *C07C 51/353* (2013.01); *C07C 67/343* (2013.01); *C07C 2529/00* (2013.01)

(58) Field of Classification Search
CPC ............................ C07C 51/353; C07D 493/08
USPC .......................................... 549/463; 562/509
See application file for complete search history.

(56) References Cited

U.S. PATENT DOCUMENTS

| | | | |
|---|---|---|---|
| 2,781,407 | A | 2/1957 | Schmerling |
| 6,677,464 | B2 | 1/2004 | Kuwayama et al. |
| 7,262,299 | B2 | 8/2007 | Caplan et al. |
| 7,385,081 | B1 | 6/2008 | Gong |
| 8,133,289 | B2 | 3/2012 | Gruter et al. |
| 8,231,693 | B2 | 7/2012 | Gruter |
| 8,242,293 | B2 | 8/2012 | Gruter et al. |
| 8,277,521 | B2 | 10/2012 | Gruier |
| 8,299,278 | B2 | 10/2012 | Gong |
| 8,314,260 | B2 | 11/2012 | Gruter et al. |
| 8,314,267 | B2 | 11/2012 | Brandvold |
| 8,338,626 | B2 | 12/2012 | Gruter et al. |
| 8,435,313 | B2 | 5/2013 | Gruter et al. |
| 8,519,167 | B2 | 8/2013 | Diego et al. |
| 8,865,921 | B2 | 10/2014 | Diego et al. |
| 8,877,950 | B2 | 11/2014 | Gruter et al. |
| 2010/0331568 | A1 | 12/2010 | Brandvold |

FOREIGN PATENT DOCUMENTS

| | | |
|---|---|---|
| EP | 22200221 B1 | 8/2012 |
| WO | WO 2014-065657 | 5/2014 |
| WO | WO 2014/197175 | 12/2014 |

OTHER PUBLICATIONS

Bilović et al., "A Novel of Intramolecular Diels-Alder Reaction in the Furan Series", Tetrahedron Letters, 1964, 31, 2071-2074.
Blasco et al., "Unseeded Synthesis of Al-free Ti-β Zeolite in fluoride Medium: A Hydrophoic Selective Oxidation Catalyst", Chem. Commun., 1996, 102, 2367-2368.
Blasco et al., "Direct Synthesis and Characterization of Hydrophobic Aluminum-Free Ti-Beta Zeolite", J. Phys. Chem. B, 1998, 102(1), 75-88.
Boronat et al., "Mechanism of the Meerwein-Ponndorf-Verley-Oppenauer MPVO) Redox Equilibirum on Sn- and Zr-Beta Zeolite Catalysts", J. Phys. Chem. B, 2006, 110(42), 21168-21174.
Brice et al., "The Kinetics of an Acid Catalyzed Aromatic Cyclodehydration Reaction in Acetic Acid-Water Mistures", J. Am. Chem. Soc., 1960, 82, 2669-2670.
Cannell, "Cyclodimerization of Ethylene and 1,3-Butadiene to Vinylcyclobutane. Homogenous Titanium Catalysts", J. Am. Chem. Soc., 1972, 94(19), 6867-6869.
Chang et al., "Rapid Dynthesis of Sn-Beta for the Isomerization of Cellulosic Sugars", RSC Advances, 2012, 2, 10475-10477.
Collias et al., "Biobased Teraphthalic Acids Technologies: A Literature Review", Industrial Biotechnology, 2014, 10(2), 91-105.
Cramer, "Transition Metal Catalysis Exemplified by Some Rhodium-Promoted Reactions of Olefins", Acc. Chem. Res., 1968, 1(6), 186-191.
Dessau et al., "Catalysis of Diels-Alder Reactions by Zeolites", J. Chem. Soc., Chem. Commun., 1986, 1167-1168.
Fraile et al., "$ZnCl_2$, $ZnI_2$, and $TiCl_4$Supported on Silican Gel As Catalysts for the Diels-Alder Reactions of Furan", J. Mol. Catal. A: Chem., 1997, 123(1), 43-47.
Friedrich et al., "Reaction of Ethylene with $C_{18}$ Monocarboxylic Dionic Acids", J. Am. Oil Chem. Soc., 1962, 1 page.
Fringuelli et al., "The Diels-Alder Reaction: Selected Practical Methods", Wiley and Sons, 2002, 350 pages.
Gandini et al., "The Furan Counterpart of Poly(ethlylene terephthalate): An Alternative Material Based on Renewable Resources", J. Polm. Sci. Part A: Polym. Chem., 2009, 47(1), 295-298.
Gomez et al., "Use of Different Microporous and Mesoporous Materials as Catalyst in the Diels-Alder and Retro-Diels-Alder Reaction Between cyclopentadiene and p-benzoquinone Activity of Al-, Ti- and Sn-doped Silica", J. of Mol. Catalysis A: Chemical, 2005, 240, 16-21.

(Continued)

*Primary Examiner* — Taofiq A Solola
(74) *Attorney, Agent, or Firm* — Baker & Hostetler LLP

(57) ABSTRACT

The present disclosure is related to silica-based Lewis acid catalysts, being essentially devoid of strong Brønsted acid character, and their ability to effect the [4+2] cycloaddition and dehydrative aromatization of dienes and dienophiles containing oxygenated substituents to form substituted benzene products. In some embodiments, the processes comprise contacting biomass-derived substrates with ethylene to form terephthalic acid and its derivatives.

35 Claims, 8 Drawing Sheets

(56) References Cited

OTHER PUBLICATIONS

Gordon et al., "A Facile, Protic Ionic Liquid Route to N-substituted 5-hydroxy-4-methyl-3-oxoisoindoline-1-carboxamides and N-substituted 3-oxoisoindoline-4-carboxylic acids", Green Chem., 2010, 12, 1000-1006.

Iwamoto et al., "Structure of Poly(ethylene oxide) complexes. II. Poly(ethlene oxide)—Mercuric Chloride Complex", J. Poly. Sci. Part A: Polym. Chem, 1968, 6(8), 1509-1525.

Jana et al., "Tandem furo[3,4-b]pyridine Formation-Diels-Alder Reaction: An Approach to the Synthesis of Nitrogen Containing Heterocyclic Analogues of 1-arylnaphthalene Ligans", Tetrahedron, 2007, 63(48), 12015-12025.

Joshel et al., The Synthesis of Condensed Ring Compounds. VII. The Successful Use of Ethylene in the Diels-Alder Reaction:, J. Am. Chem. Soc., 1941, 63(12), 3350-3351.

Keay et al., "Anamalous 5-endo-trig Reversals: General Reactions of 7- oxabicyclo[2.2.1]heptenes and heptanes", Can. J. Chem., 1984, 62, 1093-1096.

Kuczenski et al., "Material Flo Analysis of Polyethylene Terephthalate in the US, 1996-2007", Res. Conserv. Recycle, 2010, 54(12), 1161-1169.

Lew, "Tin-Containing Zeolite for the Isomerization of Cellulosic Sugars", Micro. And Meso. Matls., 2012, 55-58.

Lin et al., "Aromatics from Lignocellulosic Biomass: Economic Analysis of the Production of p-Xylene from 5-Hydroxymethylfurfural", AIChE Journal, 2013, 59(6), 2079-2087.

Mance et al., "New Compounds in Ring-Opening Reaction of 5-Substituted Epoxyisoindolines", J. Hetrocyclic Chem., 2002, 39, 277-285.

Maxwell et al., "Copper-Exchanged Zeolite Catalysts for the Cyclodimerization of Budadiene: I. Catalyst stability and Regenerability", J. of Catal., 1980, 61(2), 485-492.

Mir et al., "Synthesis and Antimicrobial Actity of Some methyl-2[N-coumarin-6'-yl]-3-oxo-2,3-dihydro-1H-isoindolone-t-carboxylates", J. Heterocyclic Chem., 2010, 47(1), 214-218.

Moliner et al., "Tin-Containing Zeolites are Highly Active Catalysts for the Isomerization of Glucose in Water", PNAS, 2010, 107(14), 6164-6168.

Moore et al., "Catalyzed Addition of Furan With Acrylic Monomers", J. Org. Chem., 1983, 48(7), 1105-1106.

Nikbin et al., "A DFT Study of the Acid-Catalyzed Conversion of 2,5-Dimethylfuran and Ethylene to P-Xylene", J. Catalysis, 2012, 1-9, http://dx.doil.org/10.1016/j.cat2012.09.017.

Nikolla et al., "One-Pot Synthesis of 5-(Hydroxymethyl)furfural from Carbohydrates Using Tin-Beta Zeolite", ACS Catalysis, 2011, 1, 408-410.

Nudenberg et al., "3,6-Epoxycyclohenexe from Furan and Thylene", J. Am. Chem. Soc., 1944, 66(2), 307-308.

Román-Leshkov et al., "Activation of Carbonyl-Containing Molecules with Solid Lewis Acids in Aqueous Media", ACS Catalysis, 2011, 1, 1566-1580.

Serrano et al., "Evidence of Solid-Solid Transformations During the TS-1 Crystallization from Amophous Wetness Impregnated $SiO_2TiO_2$ Xerogels", Microporous Materials, 1996, 7(6), 309-321.

Shiramizu et al., "On the Diels-Alder Approach to Solely Biomass-Derived Polyethylene Teraphthalate (PET): Conversion of 2,5-Dimethylfuran and Acrolein into p-Xylene", Chem. Eur. J., 2011, 17(44), 12452-12457.

Tolman, "Chemistry of tetrakis(triethyl phosphite) nikel hydride, Hni[P(OET)3]4+. III. Proton Nuclear Magnetic Resonance Study of Reactions with Dienes", J. Am. Chem. Soc., 1970, 92(23), 6785-6790.

Tuel et al., "Zirconium Containing Mesoporous Silicas: New Catalysts for Oxidation Reactions in the Liquid Phase", Chem. Comm., 1996, 5, 651-652.

Williams et al., "Cycloaddition of Biomass-Derived Furans for Catalytic Production of Renewal p-Xylene", ACS Catalysis, 2012, 2(6), 935-939.

Zhu et al., "Al-free Zr-zeolie beta as a Regioselective Catalysts in the Meerwein-Pondorf-Verley Reaction", Chem. Comm., 2003, 21, 2734-2735.

Zubkov et al., "Aromatization of IMDAF Adducts in Aqueous Alkaline Media", RSC Advances, 2012, 2(10), 4103-4109.

Zubkov et al., "An Efficient Approach to Isoindolo[2,1-b][2]benzazepines Via Intramolecular [4+2] Cycloaddition Maleic Anhydride to 4-⊕-furyl-4-N-benzalaminobut-1-enes", Tetrahedron, 2004, 60(38) 8455-8463.

Carrillo et al. (Attanasi, Ed.), "Application of microwave Irradiation, solid Supports and catalysts in Environmentally Benign Heterocyclic Chemistry", Targets in Heterocyclic Systems: Chemistry and Properties, 2003, vol. 7, p. 70.

Chang et al, "Ultra-Selective Cycloaddition of Dimethylfuran for Renewable p-xylene with 11-BEA", Green Chem., 16, 585-588, Published online: May 21, 2013.

Dias et al, 'Chiral Lewis Acid Catalysis in Diels-Alder Cycloadditions: Mechanistic Aspects and Synthetic Applications of Recent Systems', Braz. Chem. Soc., 1997, 8(4), 289-332.

Guisnet, M. And Guidotti, M., (Chester, Ed.), "Applications in Synthesis of Commodities and Fine Chemicals", Zeolite Charaterization and Catalysis, 2009, p. 311, fig. 8.21.

Hoz et al, (Rahman Ed.), "Activation of Organic Reactions by Micorwaves" Advances in Organic Synthesis, vol. 1. Modern Organofluorine Chemistry-Synthetic Aspects, 2005, p. 134, Scheme 23.

International Patent Application No. PCT/US2014/038696: International Search Report and Written Opinion dated Nov. 25, 2014, 13 pages.

Meuzelaar et al. "Diels-Alder Reactions of Carbonyl-Containing Dienophiles Catalyzed B'Tungstophosphoric Acid Supported on Silica Gel", Catalysis Letters, 1998, 56, 49-51.

Ziarani et al, "A Study of the Diastereoselectivity of Diels-Alder Reactions on the Ce-Si02 as Support", Bull. Korean Chem. Soc.. 2008, 290, 47-50.

DIELS-ALDER REACTIONS CATALYZED BY LEWIS ACID CONTAINING SOLIDS: RENEWABLE PRODUCTION OF BIO-PLASTICS

CROSS REFERENCE TO RELATED APPLICATIONS

This application claims priority to U.S. Application Nos. 61/936,213, filed Feb. 5, 2014; 61/909,131, filed Nov. 26, 2013; and 61/831,999, filed Jun. 6, 2013; all of which are incorporated by reference herein in their entireties.

TECHNICAL FIELD

This disclosure is related to the formation of terephthalic acid and related compounds and intermediates by the Lewis acid catalyzed cycloaddition of optionally substituted furans and olefins, said furans optionally derived from biomass sources.

BACKGROUND

Terephthalic acid (PTA) is one of the monomers used for the synthesis of the polyester, polyethylene terephthalate (PET), that is used for the large-scale manufacture of synthetic fibers and plastic bottles. PTA is largely produced from the liquid-phase oxidation of petroleum-derived p-xylene (PX). However, there are now ongoing worldwide efforts exploring alternative routes for producing PTA from renewable, biomass resources.

An important biomass-derived furan, 5-hydroxymethylfurfural (HMF), is a valuable platform chemical being considered for the production of many fuels and chemicals, and can be obtained from glucose and other biomass feedstocks. HMF is now being manufactured at the commercial scale in Europe at 20 tons annually using a hydrothermal process. Thus, finding efficient routes to PTA from HMF is of great interest.

One approach to the synthesis of biomass-derived PTA has been to use a Diels-Alder reaction between a biomass-derived furanic diene and a dienophile as a way to build the six carbon ring necessary for the synthesis of PTA. The Diels-Alder adduct is an oxabicyclic intermediate that must be further dehydrated to achieve the aromatic product. Diels-Alder routes to PTA from HMF have been investigated, and typically, they require the hydrogenation of HMF to 2,5-dimethylfuran (DMF). It is known that DMF and ethylene can react to form p-xylene in a one-pot Diels-Alder-dehydration reaction (see FIG. 1, top reaction scheme). This reaction has received much attention recently, and it is catalyzed by homogeneous Lewis acids and a wide variety of heterogeneous, Brønsted acid-containing solids. Although nearly 100% p-xylene yields from the Diels-Alder-dehydration reaction can be achieved, the reduction step to convert HMF to DMF requires expensive metal catalysts and a hydrogen source, making this route challenging to commercially implement. Therefore, the discovery of routes to PTA from HMF that avoid any hydrogenation steps could be useful.

Another oxidation route to PTA that has previously been considered is the Diels-Alder-dehydration reaction of ethylene with the fully oxidized HMF, 2,5-furandicarboxylic acid (FDCA). This reaction is extremely slow and only negligible yields have been reported. The unreactivity of FDCA in the Diels-Alder-dehydration reaction is presumably due to the strong electron-withdrawing effects of the two carboxyl (—$CO_2H$) groups that result in a very electron-poor and deactivated diene.

There is significant interest and a high need in the synthesis of renewable, biomass-derived terephthalic acid.

SUMMARY

Current, plant-based PET is produced from biomass-derived ethylene glycol (the PTA used is not from biomass). In order to have a 100% biomass-derived PET, PTA must be produced from biomass. Here, pathways for the production of renewable PTA, using Diels-Alder reactions between ethylene and oxidized derivatives of HMF, a biomass-derived chemical, are reported. These pathways are enabled by new catalytic chemistry that may provide routes for the production of 100% biomass-derived PET.

More specifically, the present disclosure describes newly discovered routes to PTA starting from oxidized products of biomass-derived 5-hydroxymethylfurfural (HMF). These routes involve Diels-Alder reactions with ethylene and avoid the expensive hydrogenation of HMF to 2,5-dimethylfuran. Oxidized derivatives of HMF are reacted as is, or after etherification-esterification with methanol, with ethylene over solid Lewis acid catalysts that do not contain strong Brønsted acids in order to synthesize intermediates of PTA and its equally important diester, dimethyl terephthalate (DMT). The partially oxidized HMF, 5-(hydroxymethyl)furoic acid (HMFA) can be reacted with high pressure ethylene over a catalyst, including for example a pure-silica molecular sieve catalyst containing framework tin (e.g., Sn-Beta), to produce the Diels-Alder-dehydration product, 4-(hydroxymethyl)benzoic acid (HMBA), with high selectivity HMFA conversion under moderate conditions. If HMFA is protected with methanol to form methyl 5-(methoxymethyl)furan-2-carboxylate (MMFC), MMFC can react with ethylene in the presence of such described catalysts to produce methyl 4-(methoxymethyl)benzenecarboxylate (MMBC) in practical timeframes with good selectivity and MMFC conversion. HMBA and MMBC can then be oxidized to produce PTA and DMT, respectively. While generally described in terms of this PTA/DMT system, it should be appreciated that the methods described herein are also generally applicable to other Diels Alder reactants and reactions, and as such represents an exciting new catalyst system for this important organic transformation.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, processes, devices, and systems disclosed. In addition, the drawings are not necessarily drawn to scale. In the drawings.

vide for routes involving the Diels-Alder [4+2]-cycloaddition between ethylene and a furan compound, and subsequent dehydrative aromatization to give the aromatic compound. Exemplary pathways are shown in the Scheme below:

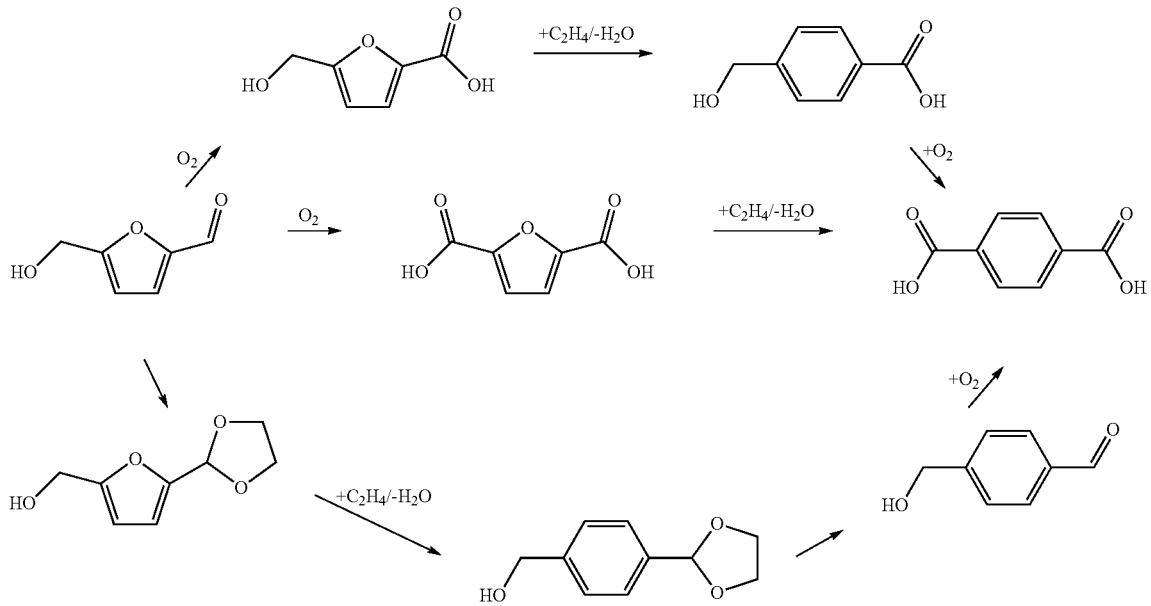

Figure 6:
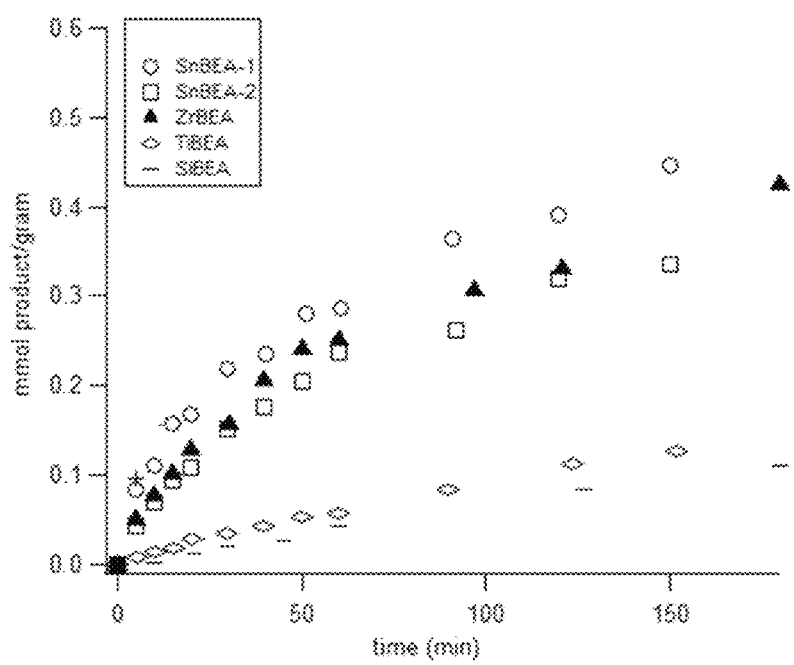

FIG. 6 traces the reactant and product concentrations with time for the Diels-Alter reaction between furan and acrylic acid using four difference BEA catalysts. T=50° C., 3.0 g furan, 0.3 g acrylic acid, 360 acrylic acid:metal molar ratio. Sn-BEA-2 profile used 784 acrylic acid:metal molar ratio, as described in Example 3.2.

Figure 7:
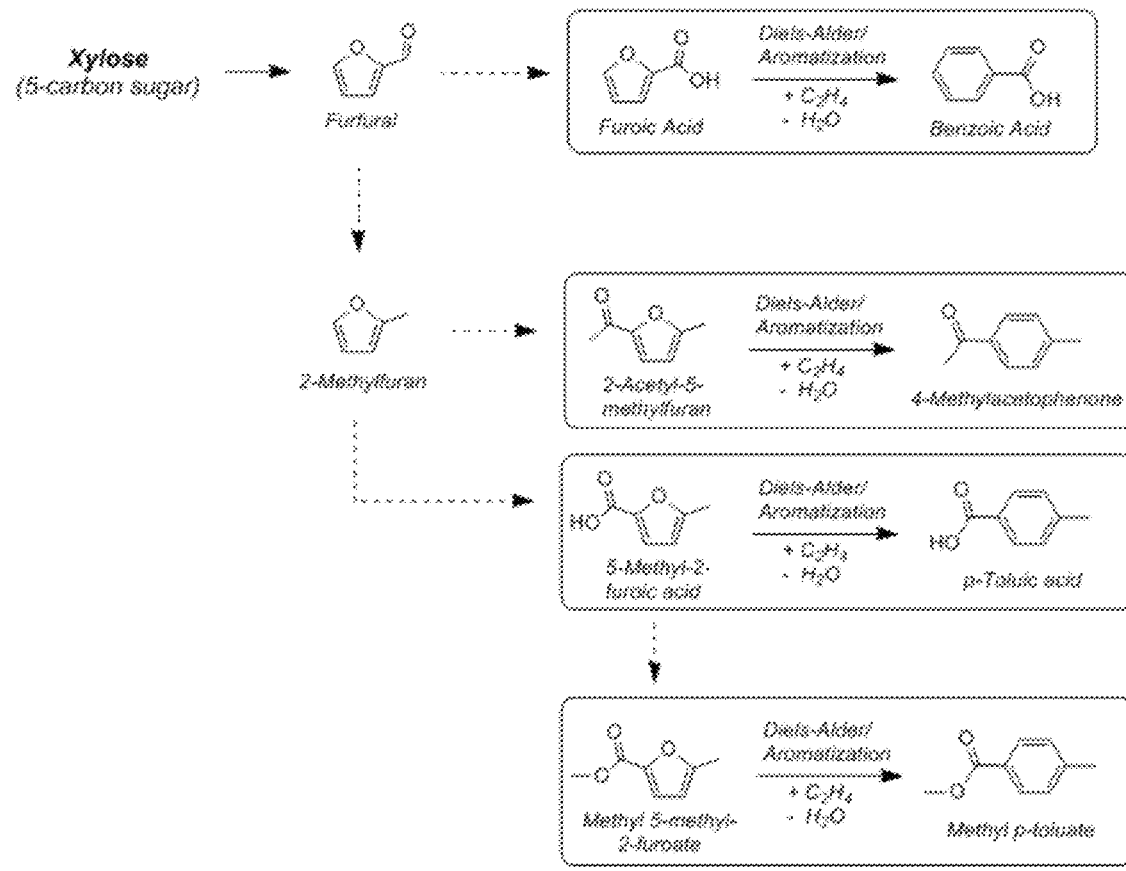

FIG. 7 illustrates several additional chemical routes to various aromatic chemicals derived from biomass.

Figure 8:
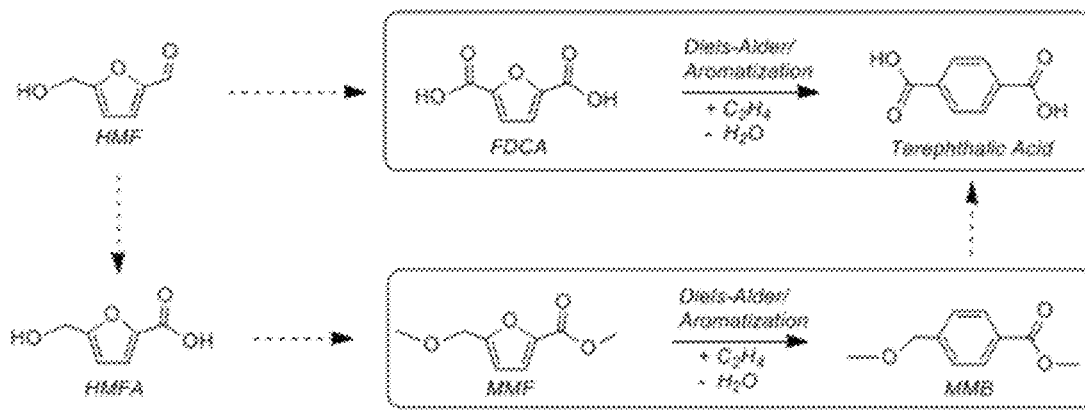

FIG. 8 illustrates two exemplary chemical routes to terephthalic acid from glucose.

Figure 9:
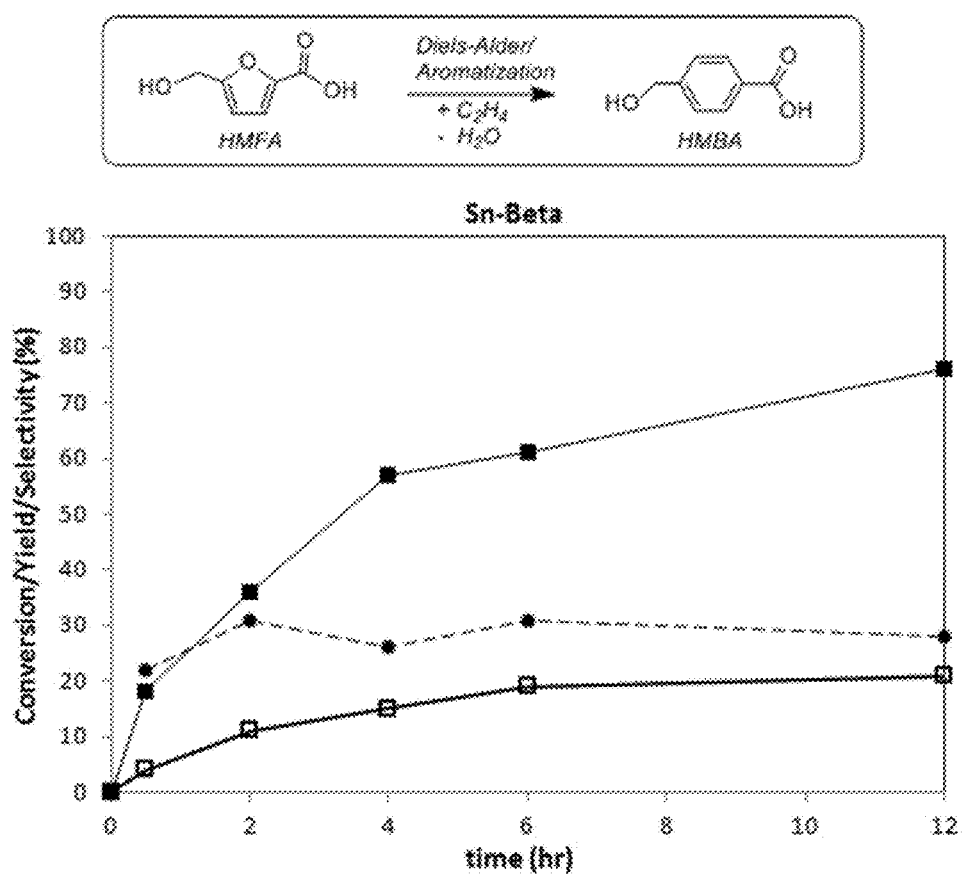

FIG. 9 illustrates the progression with time of conversion, yield, and selectivity for the reaction of HMFA to form HMBA, using 1000 psig ethylene at 190° C., 10 g of a 100 mM dioxane solution of HFMA, with 100 mg Sn-Beta catalyst, as described in Example 4.6.

Figure 10A:
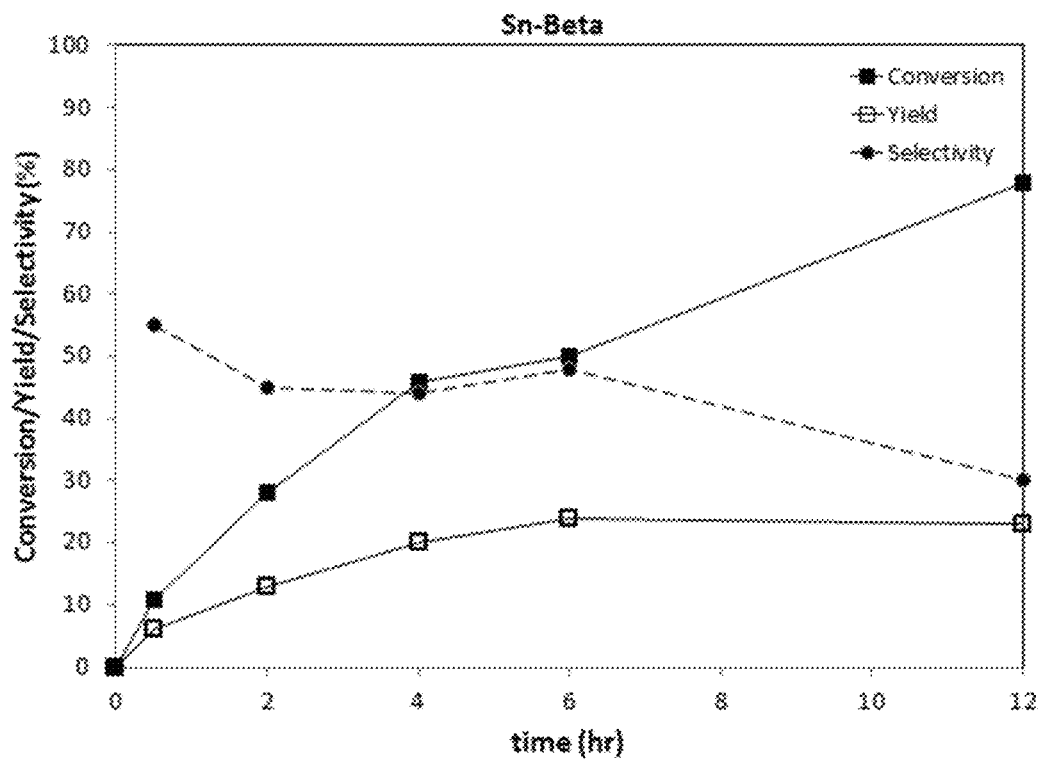
Figure 10B:
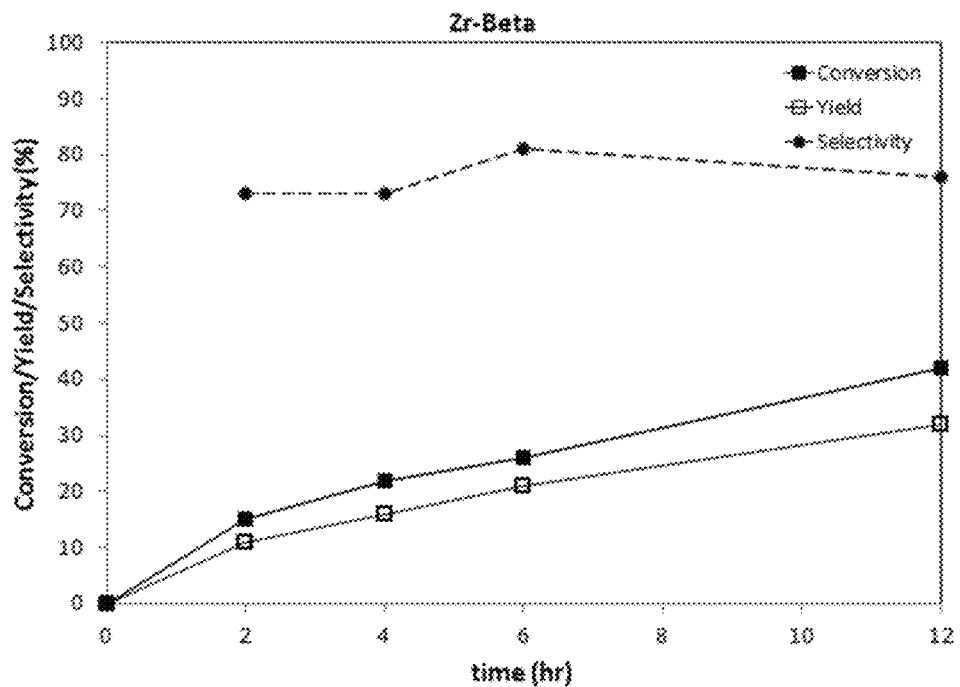

FIG. 10 illustrates the MMFC conversion (filled squares) and MMBC yield (open squares) and selectivity (circles) as a function of time at 190° C. using Sn-Beta (FIG. 10A) and Zr-Beta (FIG. 10B) as catalysts. Experiments were carried out with 1000 psig of ethylene gas and reactor was charged with 10 g of a 0.1 M (100 mM) solution of MMFC in dioxane and 100 mg of catalyst, as described in Example 4.9.

DETAILED DESCRIPTION OF ILLUSTRATIVE EMBODIMENTS

The present invention is directed to processes for the catalytic cycloaddition of optionally substituted dienes and optionally substituted dienophiles, including optionally substituted furans with optionally substituted ethylene, and further including biomass-derived materials. Specific embodiments provide for the conversion of 5-hydroxymethyl-2-furfural (HMF) and its derivatives to terephthalic acid (PTA, sometimes known as, TPA) which avoids the reduction step of HMF to dimethylfuran (DMF). Various embodiments pro- In one route, HMF is first air oxidized (or oxidized using other mild oxidants), either to 5-hydroxymethyl-2-furoic acid (HMFA) or to 2,5-furan dicarboxylic acid (FDCA). HMFA or FDCA then undergoes a cycloaddition with ethylene, and subsequent dehydrative aromatization, ultimately giving the target molecule terephthalic acid. Another pathway involves converting the aldehyde function on HMF to an acetal, at which point the Diels-Alder/aromatization steps occur. Regeneration of the aldehyde, followed by an oxidation step, gives terephthalic acid. In each pathway, the hydrogenation of HMF to DMF will be unnecessary, and due to the high atom efficiency by utilizing ethylene as the dienophile, additional steps like decarboxylation will be avoided. When these pathways are combined with ethylene produced from the dehydration of bio-ethanol, these new routes starting from HMF could provide a completely renewable source of PTA.

Figure 1:
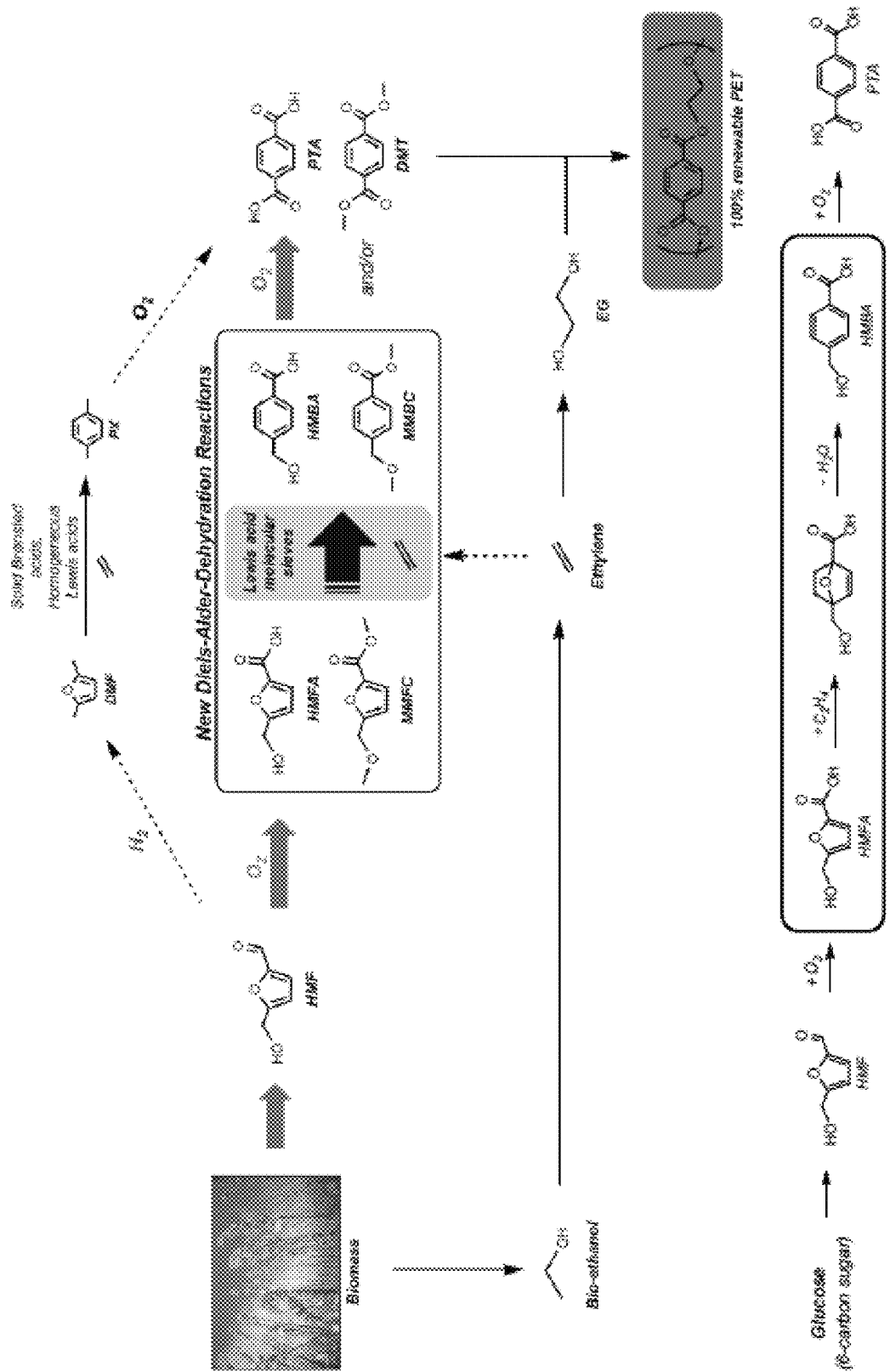
FIG. 1 illustrates several Diels-Alder pathways to purified teraphthalic acid (PTA) and dimethyl teraphthalate (DMT) starting from biomass-derived HMF using either reduction or oxidation steps.

This disclosure describes new catalytic Diels-Alder-dehydration routes to produce PTA and the equally important diester of PTA, dimethyl terephthalate (DMT), beginning with the oxidation, rather than the reduction, of HMF. The partially oxidized HMF, 5-(hydroxymethyl)furoic acid (HMFA), and each of the ether and ester derivatives of HMFA, are shown to react with ethylene in a one-pot Diels-Alder-dehydration reaction to produce the desired aromatic product (FIG. 1A/B). The aromatic products of these reactions can be oxidized to produce PTA or DMT. Since HMFA can be formed easily and in quantitative yields through the air oxidation of HMF, HMFA is a much more attractive diene than DMF for the ethylene Diels-Alder-dehydration step to produce the PTA intermediate.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) to convert a diene to a product of cycloaddition that has optionally been further dehydratively aromatized.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

While certain embodiments refer to the conversion of substituted furans to substituted benzene derivatives, and these are further discussed herein, the discovery of the present systems is believed to have much broader applicability, generally to many different types of so-called Diels-Alder [4+2] cycloadditions, and the general reactivity of these described systems and their associated processes are considered within the scope of the present disclosure. For example, various embodiments of the present invention provide methods or processes for catalyzing the cycloaddition (specifically, a [4+2] cycloaddition) between a conjugated diene, such as described in Formula (A):

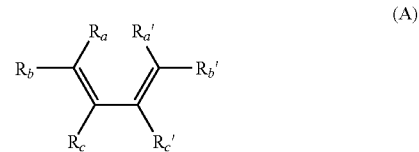

(A)

and an optionally mono-, di-, tri-, or tetra-substituted dienophile, for example as shown in Formulae B or C for an optionally di-substituted dienophile,

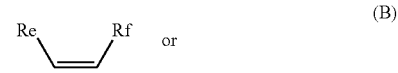

(B)

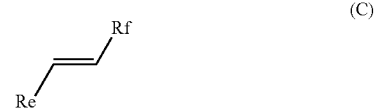

(C)

to form a substituted cyclohexene system, such as shown in Formula D,

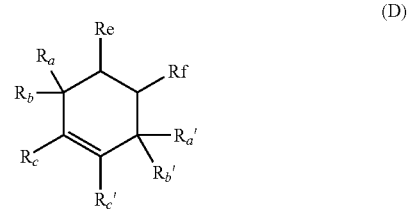

(D)

said method comprising contacting the conjugated diene and the optionally substituted dienophile in a non-aqueous solvent in the presence of a solid, silica-based Lewis acid catalyst that is essentially devoid of strong Brønsted acid character under conditions sufficient to produce the cycloaddition product; said catalyst characterized as having a +4 framework metal ion;

wherein $R_a$, $R_a'$, $R_b$, $R_b'$, $R_c$, $R_c'$ $R_d$, $R_d'$, $R_e$, and $R_f$ are independently at each occurrence H, optionally substituted alkyl, optionally substituted alkoxy, optionally substituted aryl, optionally substituted aryloxy, optionally substituted aralkyl, optionally substituted heteroalkyl, optionally substituted heteroaryl, optionally substituted heteroaryloxy, optionally substituted acyl, optionally substituted acyloxy, optionally protected hydroxy, acetal, optionally protected aldehyde, optionally protected hydroxymethyl, alkoxymethyl, optionally protected hydroxycarbonyl, alkoxycarbonyl; or Ra and Ra' together form —O—, —S—, or —N(R)—, where R is H, alkyl, or aryl. It is appreciated that the processing involving materials when Ra and Ra' together form —O— are the substituted furan systems further discussed herein. Further, when Ra and Ra' together form —O—, and the starting materials comprise substituted furans, the resulting product of Formula D may further be dehydrated and aromatized to form the corresponding benzene derivative.

As used herein, the terms "methods" or "processes" may be used interchangeably.

In certain of these embodiments, at least one of $R_a$, $R_a'$, $R_b$, $R_b'$, $R_c$, $R_c'$, $R_d$, $R_d'$, $R_e$, and $R_f$ is an oxygenated functional group. This class of oxygenated functional group includes acetal, aldehyde [—C(O)H or protected aldehyde, acyl [—C(O)-(alkyl)] or protected acyl, hydroxycarbonyl [—C(O)OH], alkoxycarbonyl [—C(O)O-(alkyl)], hydroxymethyl [—CH$_2$OH] or alkoxymethyl [—CH$_2$O(alkyl)]. In other embodiments, at least one of $R_a$, $R_a'$, $R_b$, $R_b'$, $R_c$, $R_c'$ $R_d$, $R_d'$, $R_e$, and $R_f$ is alkyl.

The solid silica-based Lewis-acid catalyst may comprise a variety of structural forms, including those having a molecular sieve structure. As will be discussed further herein, certain preferred embodiments include those processes comprising the use of silica-based molecular sieves having a *BEA topology. These and other silica-based catalysts may be characterized as having a +4 framework metal ion. In some embodiments, the solid silica-based Lewis-acid catalyst comprises Ge, Hf, Nb, Sn, Ta, Ti, Zr, or a combination thereof, preferably Sn, Ti, Zr, or a combination thereof, where the combination of metals may be tetrahedrally coordinated within the solid silica-based Lewis-acid catalyst framework. Exemplary catalyst sieve structures include those comprising meso- or microporous structures, including M-BEA, or similar frameworks, where M is Sn, Ti, Zr, or a combination thereof. In such structures, the ratio of Si to M may vary within in a range of from about 50:1 to about 250:1.

Exemplary reactions conditions include those wherein the diene and the dienophile are dissolved, dispersed, or suspended in a solvent. As will also be discussed further, the processes have been found to work well in non-aqueous, aprotic solvents, preferably cyclic ethers or lactones, and in certain preferred embodiments, solvents comprising 1,4-dioxane are preferred.

Exemplary reactions conditions also include those where the reactions are conducted at at least one temperature in a range of from about 50° C. to about 300° C. or 135° C. to about 250° C., preferably in a range of from about 150° C. to about 220° C. Typical reaction pressures for reactions employing ethylene or other volatile dienophiles include those where the total pressures is in a range of from about 800 psig to about 1200 psig.

Certain preferred embodiments of the present disclosure include those processes comprising contacting a compound of Formula (1):

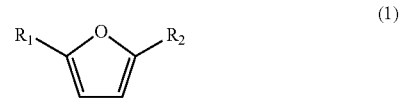

(1)

with a compound of Formula (2):

(2)

in a non-aqueous solvent in the presence of a solid, silica-based Lewis acid catalyst that is essentially devoid of strong Brønsted acid character; under conditions sufficient to produce a compound of Formula (3) or Formula (4) or both:

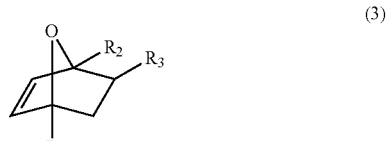

(3)

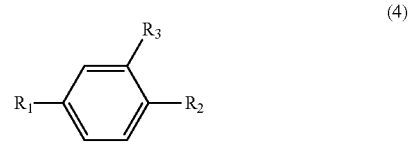

(4)

wherein $R_1$ and $R_2$ are each independently H, alkyl, or an oxygenated functional group, wherein at least one of $R_1$ or $R_2$ is the oxygenated functional group;
wherein $R_3$ is H, alkyl, or an oxygenated functional group;
wherein said oxygenated functional group is an acetal, aldehyde [—C(O)H], protected aldehyde, acyl [—C(O)-(alkyl)], protected acyl, hydroxycarbonyl [—C(O)OH], alkoxycarbonyl [—C(O)O-(alkyl)], hydroxymethyl [—CH$_2$OH] or alkoxymethyl [—CH$_2$O(alkyl)].

The structures of Formula (3) are sometimes referred to as substituted 7-oxa-bicyclo[2.2.1]hept-2-enes. The compounds of Formula (1) and (2) may be derived from biomass.

Additional embodiments include those where the dienophile is described in terms of Formula (2A) or (2B), where $R_4$ is H, alkyl, or an oxygenated functional group, such that the resulting product is a compound of Formula (3A) or (3B) or Formula (4A) or (4B), or a combination thereof

(2A)

(2B)

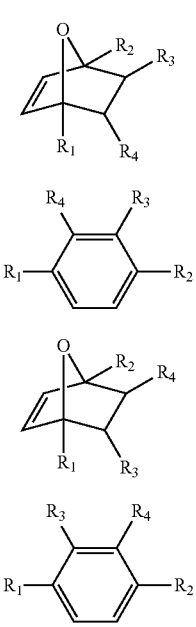

(3A)

(4A)

(3B)

(4B)

While it is believed that the processes are flexible in their choice of dienophiles, in preferred commercial embodiments, $R_3$ (and $R_4$) is H; i.e., the dienophile of Formula (2) (or (2A) or 2B)) is ethylene.

The nature of the diene and dienophile, and the nature of the reaction conditions, influences the nature and/or distribution of the products of Formulae (3) or (4) (or 3A/B vs. 4A/B). It should be appreciated that the conversion of the substituted 7-oxa-bicyclo[2.2.1]hept-2-enes of Formula (3) to the substituted benzenes of Formula (4) involves the formal dehydrative aromatization of the former to the latter, e.g.:

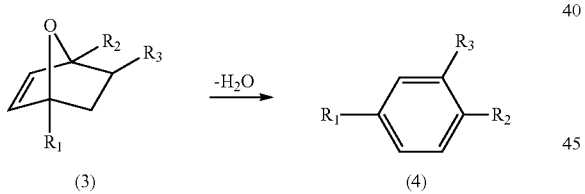

Without intending to be bound by the correctness or incorrectness of any particular theory, it is believed that the compounds of Formula (3) are first formed intermediates of the inventive processes, which subsequently react to form the compounds of Formula (4) under the reaction conditions. In any case, this conversion may be accomplished either in situ under the reaction conditions of the cycloadditions, or may be separately accomplished in a subsequent step. The present disclosure considers each of these to be separate embodiments. In certain of these embodiments, the compound of Formula (3) is formed without the detectable presence of a corresponding compound of Formula (4). In such cases, further embodiments provide that the compounds of Formula (3) may be isolated and optionally purified by conventional purification methods appropriate to the product. In still other embodiments, the compound of Formula (4) is formed without the detectable presence of a corresponding compound of Formula (3). In such cases, further embodiments provide that the compounds of Formula (4) is isolated and optionally purified by conventional purification methods appropriate to the product. As used herein, and unless otherwise indicated, the term "isolated" means physically separated from the other components so as to be free of solvents or other impurities (or as free of these extraneous materials as practicably possible). Other specific additional embodiments include those where the compound is substantially the only solute in a solvent or solvent fraction, such a analytically separated in a liquid or gas chromatography phase.

In those embodiments where the product is separated or isolated, this may be accomplished by a unit operation comprising filtration, crystallization, freeze-thawing, chromatographic separation (i.e., employing a column capable of separating the desired product from other reactants and products), solvent removal (e.g., using a centrifugal evaporator), or a combination thereof. The specific methods or processes depend on the reaction conditions employed (e.g., the levels of the product, reactant, co-product, or byproduct in the reaction mixture relative to the amount of solvent), the specific nature of the catalyst, the desired purity, or a combination thereof. It would be well within the skill of the person of ordinary skill in the art to define the process most suitable for their desired product quality.

The inventive processes have been shown to be operable on a range of substituted furan substrates, where $R_1$ and $R_2$ are each independently an oxygenated functional group. Some of these preferred precursors include compounds having the general structures:

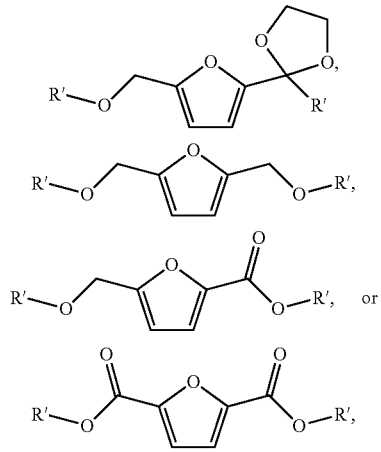

wherein R' is independently H or alkyl, or the compound of Formula

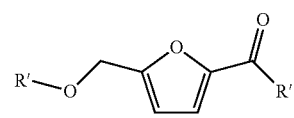

wherein R' is alkyl. While, again, the processes appear to be flexible where R' is H or alkyl, in certain independent embodiments, the corresponding alkyl group is independently $C_{1-12}$ alkyl, $C_{1-6}$ alkyl, or $C_{1-3}$ alkyl. Those embodiments where R' is independently H, methyl, or ethyl are most commercially preferred.

It should also be appreciated that the structure:

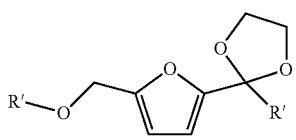

is, in addition to represent a specific embodiment itself, is representative of other protected aldehydes or ketones; i.e., alicyclic or cyclic acetals or ketals.

Initial experiments have shown that 5-hydroxymethyl-2-furfural (HMF), structurally represented as:

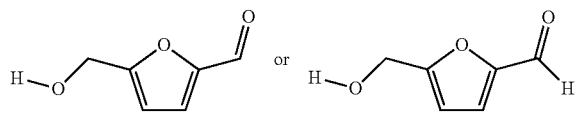 [SMILES: O=Cc1ccc(CO)o1 ; O=Cc1ccc(CO)o1]

is a particularly difficult reactant (see, e.g., Example 4.2). However, air oxidation of this compound can be used to generate the corresponding 5-hydroxymethyl-2-furoic acid (HMFA) or other oxidized derivative, which has been shown to work well in the inventive methods. It is expected that the reactivity of other aldehyde substrates may be likewise improved by similar oxidative pre-reactions.

Similarly, where $R_1$ and $R_2$ are each independently an acetal, aldehyde, alkoxycarbonyl, hydroxycarbonyl, hydroxymethyl, or alkoxymethyl; and $R_3$ is hydrogen, additional embodiments provide processes further comprising oxidizing the compound of Formula (4) under conditions sufficient to form terephthalic acid or an diester thereof.

In other embodiments, compounds of Formula (3) being

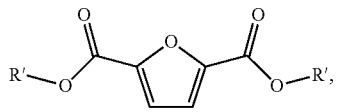

are reacted under appropriate conditions with substituted alkenes to form the corresponding para-substituted benzoic acid derivatives. When this diene is reacted with ethylene, under appropriate conditions, the processes are capable of forming

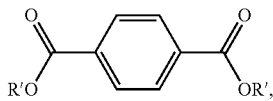

where R' are each independently H or alkyl. Again, here, preferred alkyls include $C_{1-12}$ alkyl, $C_{1-6}$ alkyl, or $C_{1-3}$ alkyl, and those embodiments where R' is independently H, methyl, or ethyl are most commercially preferred.

In still other embodiments, compounds of Formula (3) being

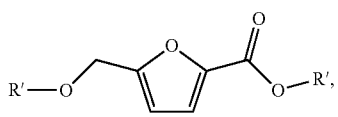

are reacted under appropriate conditions with substituted alkenes to form the corresponding para-substituted benzoic acid derivatives. When this diene is reacted with ethylene, under appropriate conditions, the processes are capable of forming

Figure 2:
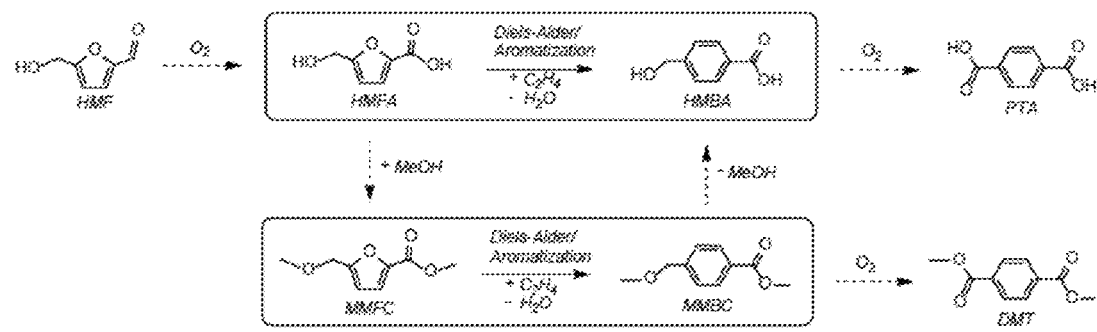
FIG. 2 provides two exemplary schemes for the conversion of 5-hydroxymethyl-2-furfural (HMF) to terephthalic acid (PTA) or dimethylterephthalate (DMT)

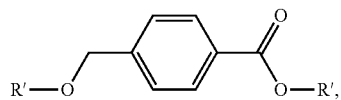

wherein R' are each independently H or alkyl. Again, here, preferred alkyls include $C_{1-12}$ alkyl, $C_{1-6}$ alkyl, or $C_{1-3}$ alkyl, and those embodiments where R' is independently H, methyl, or ethyl are most commercially preferred. Once formed, these compounds may be further oxidized to form the corresponding terephthalic acid derivatives. FIG. 2.

In yet other embodiments, compounds of Formula (3) according to:

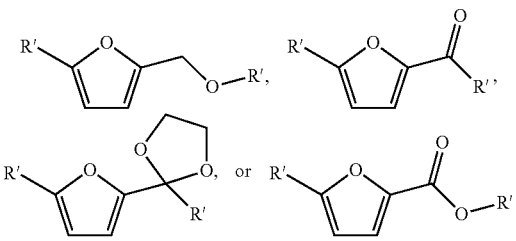

are reacted under appropriate conditions with ethylene or substituted ethylene, to form the corresponding para-substituted benzene derivatives, wherein R' are each independently H or alkyl. Again, here, preferred alkyls include $C_{1-12}$ alkyl, $C_{1-6}$ alkyl, or $C_{1-3}$ alkyl, and those embodiments where R' is independently H, methyl, or ethyl are most commercially preferred.

To this point, the catalysts of the present processes have been described in terms of a "solid, silica-based Lewis acid catalyst that is essentially devoid of strong Brønsted acid character." The term "Brønsted acid character" describes the ability of a chemical or material to donate protons under the reaction conditions. "Essentially devoid of strong a Brønsted acid character" describes a condition in which the propensity to donate protons is stronger than available from the OH of the silanol bonds of the solid, silica-based Lewis acid catalyst; e.g., Al—OH bonds have stronger Brønsted acid character than Si—OH bonds and so embodiments in this the catalysts separately have appreciable (sufficient to cause measurable decomposition of the starting materials) or any aluminum within the framework may be considered outside the scope of the present claims. In part, for this reason, the term "zeolite" is specifically avoided to describe the inventive systems, as this term connotes structures having aluminosilicate character, and the present of the alumina appears to have a deleterious effect on the quality of the reaction product. Presence of strong a Brønsted acid character causes unwanted side reactions, especially where the diene or dienophile comprises oxygenated functional groups. As shown in the Examples, the presence of significantly strong Brønsted acid causes the formation of dark brown or black, presumably decomposition, materials under conditions where the process otherwise provide good conversions and selectivities.

In certain of the embodiments described herein, the solid silica-based Lewis-acid catalyst used in the process is a molecular sieve containing a +4 framework metal ion. As used herein, the term "molecular sieve" refers to a material with very small holes of precise and uniform size. These holes are small enough to block large molecules while allowing small molecules to pass. The diameter of a molecular sieve is measured in Angstroms (Å) or nanometers (nm). According to IUPAC notation, microporous materials have pore diameters of less than 2 nm (20 Å) and macroporous materials have pore diameters of greater than 50 nm (500 Å); the mesoporous category thus lies in the middle with pore diameters between 2 and 50 nm (20-500 Å).

The term "+4 framework metal ion" refers to a metal ion within the framework of the silica-based catalyst having an nominal oxidation state of +4, or having access to an oxidation state of +4. Such metals include, for example, Ge, Hf, Nb, Pb, Sn, Ta, Ti, and Zr, and catalysts useful in the present inventive processes include these metals, either individually, or in combination with one another. These catalytic metals are best provided in the silica frameworks, there the metals are tetrahedrally coordinated within the solid silica-based Lewis-acid catalyst framework.

The processes are flexible in the atomic ratios of Si:M (where M is Ge, Hf, Nb, Pb, Sn, Ta, Ti, Zr, or combinations thereof, preferably Sn, Ti, Zr, or combinations thereof) that can be employed in the catalysts structures. In some embodiment, the silica matrices have compositions such that the atomic ratio of Si to M is in a range of from about 50:1 to about 250:1. In certain other separate embodiments, the silica-based catalyst structure has a composition such that the atomic ratio of Si to M is in a range having a lower boundary of about 50, about 65, about 80, about 100, or about 120, and the range having an upper boundary of 200, about 120, about 100, or about 80; for example Si:M being in a range of from about 65 to about 120. Non-limiting exemplary ranges, then, include from about 50 to about 65, from about 65 to about 80, from about 80 to about 110, from about 110 to about 150, from about 150 to about 200, from about 200 to about 250, or a combination thereof. Preferred embodiments include those processes wherein the solid silica-based Lewis-acid catalyst comprises Sn, Ti, Zr, or a combination thereof, and the Sn, Ti, Zr, or combination thereof is tetrahedrally coordinated within the molecular sieve. Catalysts comprising Pb are generally less preferred, on environmental grounds.

It is appreciated that various types of silica-containing structures containing Lewis acidic metal ion framework centers may be applied individually or in combination with one another, either in a serial arrangement or temporal batchwise arrangements, or both. It should also be appreciated that the cycloaddition reactions described herein are catalytic with respect to the metal-silica-containing structures.

In certain embodiments, the solid silica-based Lewis-acid catalyst comprises a microporous material. In other embodiments, the solid silica-based Lewis-acid catalyst comprises a mesoporous material. In still other embodiments, the solid silica-based Lewis-acid catalyst comprises an amorphous material.

The solid silica-based Lewis-acid catalyst may also be described as comprising a silica-based molecular sieve having a 10-membered ring topology. Such topologies generally are considered microporous, having pore sizes on the order of 5 Å. In other embodiments, the solid silica-based Lewis-acid catalyst may also be described as comprising a silica-based molecular sieve having a 12-membered-ring topology, or larger. Such topologies generally are also considered microporous, having pore sizes on the order of 7 Å. Without intending to be bound by the correctness of any particular theory, the topology of the silica-based catalyst structure having a 12 membered-ring (12-MR) or larger (which may alternatively described as providing pore sizes of 0.7 nanometers or above) is believed to be important so as to allow the reactants and products more easily to migrate in and out of the structures, respectively.

One subset of the microporous molecular sieves which appear to be especially attractive in the present processes include those where the silica-based molecular sieve has a *BEA topology. In particular, processes in which the solid silica-based Lewis-acid catalyst comprises M-BEA, where M is Sn, Ti, Zr, or a combination thereof, the ratio of Si to M is in a range of from about 50:1 to about 250:1 find particular utility As described above, other ranges for the ratio of Si to M include those from about 50 to about 65, from about 65 to about 80, from about 80 to about 110, from about 110 to about 150, from about 150 to about 200, from about 200 to about 250, or a combination thereof.

In other separate embodiments, the silica-containing structures comprise or consist essentially of an ordered or amorphous silica, again provided that the structure contains the appropriate Lewis acidic framework centers. Non-limiting examples of ordered mesoporous silica material include MCM-41, MCM-48, and SBA-15 structures. Non-limiting examples of amorphous silica-containing tin, titania or zirconia centers in amorphous silica include, for example $SnO_2$—$SiO_2$, $TiO_2$—$SiO_2$ or $ZrO_2$—$SiO_2$ (alternatively represented as Sn—$SiO_2$, Ti—$SiO_2$ or Zr—$SiO_2$) co-precipitated or formed as a mixed oxide.

The catalysts may be prepared by methods, including conventional methods, including those described and characterized in Example 1.1. Such methods may include:
  (a) mixing an appropriate amount of tetraethyl ammonium fluoride, tetraorthosilicate, and $SnCl_4$ sequentially in water, removing the solvent to form a gel, optionally seeding the gel with calcined Sn-BEA, and calcining the gel; or
  (b) mixing an appropriate amount of tetraethyl ammonium hydroxide, tetraorthosilicate, and an alcoholic solution of zirconium (IV) propoxide sequentially in water, removing the solvent to form a gel, and calcining the gel; or
  (c) mixing an appropriate amount of tetraethyl ammonium fluoride, tetraorthosilicate, and an alcoholic solution of titanium (IV) propoxide sequentially in water, removing the solvent to form a gel, and calcining the gel.

To this point, the reaction conditions have been described in terms of using a "non-aqueous solvent" and "under conditions sufficient to produce a compound of Formula (3) or Formula (4) or both." While the processes may be fairly flexible in terms of solvent choice, potentially including glyme, diglyme, cyclic ethers, lactones, ketones (e.g., $C_{3-10}$ ketone), esters, and hydrocarbons (e.g., $C_{3-12}$ aliphatic hydrocarbon solvent, or $C_{6-12}$ aromatic hydrocarbon solvents), aprotic solvents are preferred and good results have been achieved with solvents comprising cyclic ethers (e.g., 2-methyl-tetrahydrofuran, tetrahydrofuran, 1,4-dioxane) or lactones (e.g., γ-valerolactone), especially solvents comprising 1,4-dioxane. Solvents containing hydrocarbons up to about 20, 30, 40, or about 50 vol % in dioxane have also been shown to work well, and are in the scope of the present disclosure.

The processes are operable at relatively modest temperatures. In certain embodiments, the reaction conditions comprise heating the reaction mixture to at least one temperature in a range of from about 50° C. to about 300° C. or 135° C. to about 250° C., preferably in a range of from about 150° C. to about 220° C., for a time in a range of from about 2 hours to about 24 hours, or longer. Given the volatility of the solvents employed in these processes, reactions may be (and are preferably) conducted in sealed reactors, such that at least some of the local pressures are reflective of solvent boiling point. The reactions may be conducted aerobically or anaerobically—but mainly for safety reasons, anaerobic conditions are preferred. Also, depending on the nature of the dienes and/or dienophile, there may be little advantage to higher temperatures, and in some cases, lower temperatures (e.g., about 190° C.) for longer times have provided very good yields and selectivities. Generally, a programmed temperature ramp profile may be used, with ramp rates on the order of about 5° to about 15°/minutes.

Where both the diene or dienophile are solid or liquid at ambient temperature, the operating pressure of the reaction depends, at least in part, on the boiling points of either or both substrates. In the particular case of ethylene, and other substrates that are gases at or near ambient room temperatures, quantities are chosen such that the total operating pressures (solvent+ethylene+diene pressure) at the temperature of interest are in a range of from about 500 psig to about 1500 psig, though higher and lower pressures may also be used.

Depending again on the nature of the diene and dienophile, some embodiments provide processes which are operated or operable with the solid silica-based Lewis-acid catalyst under reaction conditions sufficient to convert the compound of Formula (1) to the corresponding compound of Formula (3) or Formula (4) at at least one temperature described herein, e.g., in a range of from about 145° C. to about 250° C. with (a) a product yield of at least about 10%; or (b) a selectivity of at least 30%; or (c) both (a) and (b).

Other embodiments provide processes, which are operated or operable with the solid silica-based Lewis-acid catalyst under reaction conditions sufficient to convert methyl 5-(methoxymethyl)furan-2-carboxylate (MMFC) to methyl 4-(methoxymethyl)benzenecarboxylate (MMBC) at at least one temperature described herein, e.g., in a range of about 145° C. to about 250° C. with (a) a product yield of at least about 10%; or (b) a selectivity of at least 30%; or (c) both (a) and (b).

Still other embodiments provide processes that are operated or operable with the solid silica-based Lewis-acid catalyst under reaction conditions sufficient to convert 5-(hydroxymethyl)-2-furoic acid (HMFA) to 4-(hydroxymethyl) benzoic acid (HMBA) at at least one temperature described herein, e.g., in a range of about 145° C. to about 250° C. with (a) a product yield of at least about 10%; (b) a selectivity of at least 30%; or (c) both (a) and (b).

In still other embodiments, the process comprises the use of 4-hydroxymethyl furfural (HMF) formed by the dehydration of fructose or derived from biomass, or both. This HMF material may be subjected to conditions that oxidize the aldehyde moiety to form an intermediate suitable for reaction under the conditions described.

Terms

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, or 1 to about 6 carbon atoms, 1 to about 3 carbon atoms. Certain embodiments provide that the alkyl is methyl, ethyl, n-propyl, isopropyl, n-butyl, isobutyl, tert-Butyl, octyl, decyl, or the like, as well as cycloalkyl groups such as cyclopentyl, cyclohexyl or the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and include "heteroatom-containing alkyl" and "heteroalkyl," which terms refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo" and "halogen" are used in the conventional sense to refer to a chloro, bromo, fluoro, or iodo substituent.

The term "heteroatom-containing" as in a "heteroatom-containing group" refers to a hydrocarbon molecule or molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl),N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl) substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl),N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR═NH where R =hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$OH), sulfonate ($SO_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—$B(OH)_2$), boronato (—$B(OR)_2$ where R is alkyl or aryl), phosphono (—P(O)(OH)$_2$), phosphonato (—P(O)(O)$_2$), phosphinato (P(O)(O—)), phospho (—$PO_2$), and phosphine (—$PH_2$); and the moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Where substituents are described as "substituted" or "optionally substituted," these Fn substitutions preferably comprise halo, hydroxyl, $C_1$-$C_3$ alkoxy, $C_1$-$C_6$ alkylcarbonyl (—CO-alkyl), $C_2$-$C_{24}$ alkoxycarbonyl ((CO)—O-alkyl), carboxy (—COOH), carbamoyl (—(CO)—$NH_2$), mono-($C_1$-$C_6$ alkyl)-substituted carbamoyl (—(CO)NH($C_1$-$C_6$ alkyl)), di-($C_1$-$C_6$ alkyl)-substituted carbamoyl (—(CO)—N($C_1$-$C_6$ alkyl)$_2$), cyano (—C≡N), cyanato (—O—C≡N), thiocyanato (—S—C≡N), formyl (—(CO)—H), amino (—$NH_2$), mono-($C_1$-$C_6$ alkyl)-substituted amino, or di-($C_1$-$C_6$ alkyl)-substituted amino.

By "functionalized" as in "functionalized alkyl," "functionalized olefin," "functionalized cyclic olefin," and the like, is meant that in the alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups such as those specifically enumerated above. Analogously, the above-mentioned groups may be further substituted with one or more functional groups such as those specifically enumerated.

Unless otherwise indicated, the term "isolated" means physically separated from the other components so as to be free of solvents or other impurities; additional embodiments include those where the compound is substantially the only solute in a solvent or solvent fraction, such a analytically separated in a liquid or gas chromatography phase.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2$^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003). Examples of such a protecting group, in the case of an aldehyde or ketone, include dialkylacetals or dialkyl ketals, such as dimethylacetal, and 5- or 6-membered cyclic acetals or ketals such as 1,3-dioxolane or 1,3-dioxane.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target molecule or other material may or may not be separated from other materials used or generated in the method, and, thus, the description includes separate embodiments where the target molecule or other material is separated and where the target molecule or other material is not separated, such that subsequence steps are conducted on isolated or in situ generated product.

The terms "separating" or "separated" carries their ordinary meaning as would be understood by the skilled artisan, insofar as it connotes separating or isolating the material (e.g., terephthalic acid or ester) from other starting materials or co-products or side-products (impurities) associated with the reaction conditions yielding the material. As such, it infers that the skilled artisan at least recognizes the existence of the product and takes specific action to separate or isolate it. Absolute purity is not required, though preferred, as the material may contain minor amounts of impurities and the separated or isolated material may contain residual solvent or be dissolved within a solvent used in the reaction or subsequent purification of the material.

The following listing of embodiments is intended to complement, rather than displace or supersede, the previous descriptions.

Embodiment 1. A process comprising contacting a compound of Formula (1):

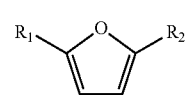

(1)

with a compound of Formula (2):

(2)

in a non-aqueous solvent in the presence of a solid, silica-based Lewis acid catalyst that is essentially devoid of strong Brønsted acid character;

under conditions sufficient to produce a compound of Formula (3) or Formula (4) or both:

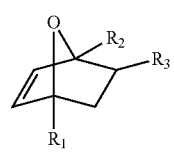

(3)

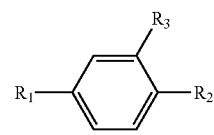

(4)

wherein $R_1$ and $R_2$ are each independently H, alkyl, or an oxygenated functional group, wherein at least one of $R_1$ or $R_2$ is the oxygenated functional group;

wherein $R_3$ is H, alkyl, or an oxygenated functional group;

wherein said oxygenated functional group is an acetal, aldehyde [—C(O)H] or protected aldehyde, acyl [—C (O)-(alkyl)] or protected acyl, hydroxycarbonyl [—C(O)OH], alkoxycarbonyl [—C(O)O-(alkyl)], hydroxymethyl [—CH₂OH] or alkoxymethyl [—CH₂O(alkyl)].

Embodiment 2. The process of Embodiment 1, wherein R₃ is hydrogen.

Embodiment 3. The process of Embodiment 1 or 2, wherein R₁ and R₂ are each independently an oxygenated functional group.

Embodiment 4. The process of any one of Embodiments 1 to 3, wherein the compound of Formula (1) is

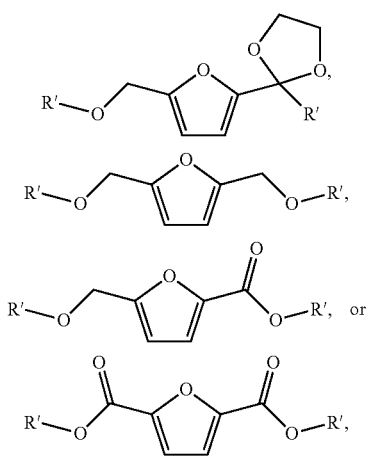

wherein R' is independently H or alkyl, especially $C_{1-3}$ alkyl, such as —CH₃ or —C₂H₅, or the compound of Formula

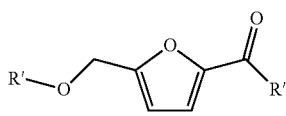

wherein R' is alkyl.

Embodiment 5. The process of any one of Embodiments 1 to 4, wherein the compound of Formula (1) is

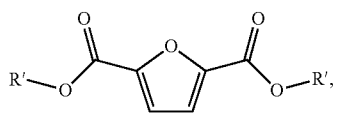

and the conditions sufficient to produce a compound of Formula (4) that is:

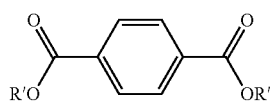

where R' are each independently H or alkyl.

Embodiment 6. The process of any one of Embodiments 1 to 4, wherein the compound of Formula (1) is

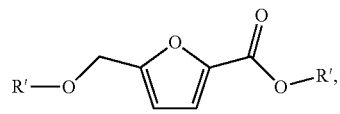

and the conditions sufficient to produce the compound of Formula (4) that is:

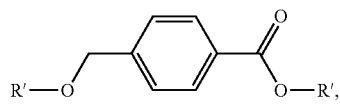

wherein R' are each independently H or alkyl.

Embodiment 7. The process of Embodiment 1 or 2, wherein the compound of Formula (1) is

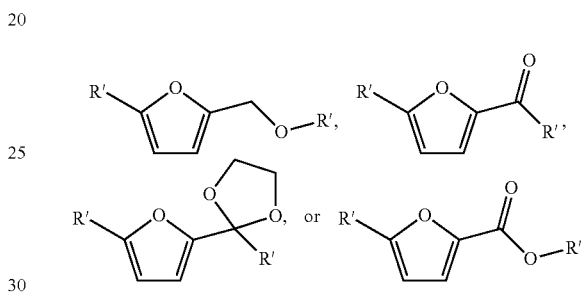

wherein R' is H or alkyl, especially $C_{1-3}$ alkyl such as —CH₃ or —C₂H₅.

Embodiment 8. The process of any one of Embodiments 1 to 7, where R₁ and R₂ are each independently an acetal, aldehyde, alkoxycarbonyl, hydroxycarbonyl, hydroxymethyl, or alkoxymethyl; and R₃ is hydrogen, said process further comprising oxidizing the compound of Formula (4) under conditions sufficient to form terephthalic acid or an diester thereof Embodiment 9. The process of any one of Embodiment 1 to 8, wherein the solid silica-based Lewis-acid catalyst is a molecular sieve.

Embodiment 10. The process of any one of Embodiments 1 to 9, wherein the solid silica-based Lewis-acid catalyst comprises a microporous material.

Embodiment 11. The process of any one of Embodiments 1 to 10, wherein the solid silica-based Lewis-acid catalyst comprises a mesoporous material.

Embodiment 12. The process of any one of Embodiments 1 to 9, wherein the solid silica-based Lewis-acid catalyst is a silica-based molecular sieve having a 10-membered ring topology.

Embodiment 13. The process of any one of Embodiments 1 to 12, wherein the solid silica-based Lewis-acid catalyst is a silica-based molecular sieve having a *BEA topology.

Embodiment 14. The process of any one of Embodiments 1 to 12, wherein the solid silica-based Lewis-acid catalyst comprises Ge, Hf, Nb, Sn, Ta, Ti, Zr, or a combination thereof Embodiment 15. The process of any one of Embodiments 1 to 14, wherein the solid silica-based Lewis-acid catalyst comprises Sn, Ti, Zr, or a combination thereof Embodiment 16. The process of Embodiment 15, wherein the solid silica-based Lewis-acid catalyst comprises Sn, Ti, Zr, or the combination thereof, and the Sn, Ti, Zr, or combination thereof is tetrahedrally coordinated within the solid silica-based Lewis-acid catalyst framework.

Embodiment 17. The process of any one of Embodiments 1 to 16, wherein the solid silica-based Lewis-acid catalyst comprises M-BEA, where M is Sn, Ti, Zr, or a combination thereof, the ratio of Si to M is in a range of from about 50:1 to about 250:1.

Embodiment 18. The process of any one of Embodiments 1 to 17, wherein the molecular sieve comprises Sn-BEA, Ti-BEA, Zr-BEA, or a combination thereof.

Embodiment 19. The process of any one of Embodiments 1 to 8, wherein the solid silica-based Lewis-acid catalyst comprises amorphous silica.

Embodiment 20. The process of any one of Embodiments 1 to 8, wherein the solid silica-based Lewis-acid catalyst comprises mesoporous silica.

Embodiment 21. The process of any one of Embodiments 1 to 20, wherein the compound of Formula (3) is isolated.

Embodiment 22. The process of any one of Embodiments 1 to 21, wherein the compound of Formula (4) is isolated.

Embodiment 23. The process of any one of Embodiments 1 to 22, wherein the compound of Formula (3) is formed without the detectable presence of a corresponding compound of Formula (4).

Embodiment 24. The process of any one of Embodiments 1 to 23, wherein the compound of Formula (4) is formed without the detectable presence of a corresponding compound of Formula (3).

Embodiment 25. The process of any one of Embodiments 1 to 24, wherein the compound of Formula (4) is formed by the in situ dehydration of a corresponding compound of Formula (3).

Embodiment 26. The process of any one of Embodiments 1 to 25, wherein the non-aqueous solvent comprises 2-methyl-tetrahydrofuran, tetrahydrofuran, or 1,4-dioxane, γ-valerolactone.

Embodiment 27. The process of any one of Embodiments 1 to 26, wherein the non-aqueous solvent comprises 1,4-dioxane.

Embodiment 28. The process of any one of Embodiments 1 to 27, wherein contacting the compound of Formula (1) and Formula (2) in the presence of the solid, silica-based Lewis-acid catalyst is done at a temperature in a range of from about 50° C. to about 300° C. or 135° C. to about 250° C., preferably in a range of from about 150° C. to about 220° C.

Embodiment 29. The process of any one of Embodiments 1 to 28, wherein contacting the compound of Formula (1) and ethylene in the presence of the solid silica-based Lewis-acid catalyst is done at a total pressure in a range of from about 500 psig to about 1500 psig (or higher).

Embodiment 30. The process of any one of Embodiments 1 to 29, wherein the solid silica-based Lewis-acid catalyst is operated under reaction conditions sufficient to convert the compound of Formula (1) to the corresponding compound of Formula (3) or Formula (4) at a temperature in a range of from about 145° C. to about 250° C. with (a) a product yield of at least about 10%; or (b) a selectivity of at least 30%; or (c) both (a) and (b).

Embodiment 31. The process of any one of Embodiments 1 to 30, wherein the solid silica-based Lewis-acid catalyst is operated under reaction conditions sufficient to convert methyl 5-(methoxymethyl)furan-2-carboxylate (MMFC) to methyl 4-(methoxymethyl)benzenecarboxylate (MMBC) at temperatures in a range of from about 145° C. to about 250° C. with (a) a product yield of at least about 10%; or (b) a selectivity of at least 30%; or (c) both (a) and (b).

Embodiment 32. The process of any one of Embodiments 1 to 31, wherein the solid silica-based Lewis-acid catalyst is operated under reaction conditions sufficient to convert 5-(hydroxymethyl)furoic acid (HMFA) to 4-(hydroxymethyl)benzoic acid (HMBA) at temperatures in a range of from about 145° C. to about 250° C. with (a) a product yield of at least about 10%; (b) a selectivity of at least 30%; or (c) both (a) and (b).

Embodiment 33. The process of any one of Embodiments 1 to 32, comprising oxidizing or converting 4-hydroxymethyl furfural (HMF), formed by the dehydration of fructose, to a compound of Embodiment 4 before contacting with the compound of Formula (2).

Embodiment 34. The process of any one of Embodiments 1 to 33, comprising oxidizing or converting 4-hydroxymethyl furfural (HMF), derived from biomass, to a compound of Embodiment 4 before contacting with the compound of Formula (2).

Embodiment 35. A method of catalyzing the cycloaddition (specifically, a [4+2] cycloaddition) between a conjugated diene, such as described in Formula (A)

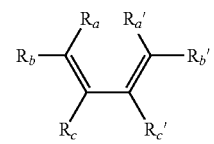

and an optionally mono-, di-, tri-, or tetra-substituted dienophile, for example as shown in Formulae B or C for an optionally di-substituted dienophile,

(B)

(C)

to form a substituted cyclohexene system,

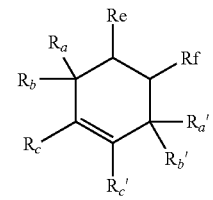

said method comprising contacting the conjugated diene and the optionally substituted dienophile in a non-aqueous solvent in the presence of a solid, silica-based Lewis acid catalyst that is essentially devoid of strong Brønsted acid character under conditions sufficient to produce the cycloaddition product; said catalyst characterized as having a +4 framework metal ion;

wherein $R_a$, $R_a'$, $R_b$, $R_b'$, $R_c$, $R_c'$ $R_d$, $R_d'$, $R_e$, and $R_f$ are independently at each occurrence H, optionally substituted alkyl, optionally substituted alkoxy, optionally substituted aryl, optionally substituted aryloxy, optionally substituted aralkyl, optionally substituted heteroalkyl, optionally substituted alkoxy, optionally substituted heteroaryl, optionally substituted heteroaryloxy, optionally substituted acyl, optionally substituted acyloxy, optionally protected hydroxy, acetal, optionally protected aldehyde, optionally protected hydroxymethyl, alkoxymethyl, optionally protected hydroxycarbonyl, alkoxycarbonyl; or Ra and Ra' together form —O—, —S—, or —N(R)—, where R is H, alkyl, or aryl.

Embodiment 36. The method of Embodiment 35, wherein the at least one of $R_a$, $R_a'$, $R_b$, $R_b'$, $R_c$, $R_c'$ $R_d$, $R_d'$, $R_e$, and $R_f$ is an oxygenated functional group.

Embodiment 37. The method Embodiment 35 or 36, wherein the oxygenated functional group is an acetal, aldehyde [—C(O)H] or protected aldehyde, acyl [—C(O)-(alkyl)] or protected acyl, hydroxycarbonyl [—C(O)OH], alkoxycarbonyl [—C(O)O-(alkyl)], hydroxymethyl [—CH$_2$OH] or alkoxymethyl [—CH$_2$O(alkyl)].

Embodiment 38. The process of any one of Embodiments 35 to 37, wherein the solid silica-based Lewis-acid catalyst is a molecular sieve.

Embodiment 39. The process of any one of Embodiments 35 to 38, wherein the solid silica-based Lewis-acid catalyst is a silica-based molecular sieve having a *BEA topology.

Embodiment 40. The process of any one of Embodiments 35 to 39, wherein the solid silica-based Lewis-acid catalyst comprises Ge, Hf, Nb, Sn, Ta, Ti, Zr, or a combination thereof Embodiment 41. The process of any one of Embodiments 35 to 40, wherein the solid silica-based Lewis-acid catalyst comprises Sn, Ti, Zr, or a combination thereof Embodiment 42. The process of Embodiments 41, wherein the solid silica-based Lewis-acid catalyst comprises Sn, Ti, Zr, or the combination thereof, and the Sn, Ti, Zr, or combination thereof is tetrahedrally coordinated within the solid silica-based Lewis-acid catalyst framework.

Embodiment 43. The process of any one of Embodiments 35 to 42, wherein the solid silica-based Lewis-acid catalyst comprises M-BEA, where M is Sn, Ti, Zr, or a combination thereof, the ratio of Si to M is in a range of from about 50:1 to about 250:1.

Embodiment 44. The process of any one of Embodiments 35 to 43, wherein the molecular sieve comprises Sn-BEA, Ti-BEA, Zr-BEA, or a combination thereof.

Embodiment 45. The process of any one of Embodiments 35 to 44, wherein the non-aqueous solvent comprises 1,4-dioxane.

Embodiment 46. The process of any one of Embodiments 35 to 45, wherein contacting the diene and the dienophile in the presence of the solid, silica-based Lewis acid catalyst is done at a temperature in a range of from about 50° C. to about 300° C. or 135° C. to about 250° C., preferably in a range of from about 150° C. to about 220° C.

Embodiment 47. The process of any one of Embodiments 35 to 46, wherein contacting the diene and the dienophile in the presence of the solid, silica-based Lewis acid catalyst is done at a total pressure in a range of from about 800 psig to about 1200 psig.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric. The term "dioxane" used throughout refers to 1,4-dioxane.

Example 1

Materials and Methods

Example 1.1

Synthesis of Catalytic Materials

Synthesis of Sn-Beta: A typical Sn-Beta molecular sieve was prepared as follows: 7.46 g of an aqueous tetraethylammonium hydroxide (TEAOH) solution [Sigma-Aldrich, 35% (wt/wt)] was diluted with 15 g of water. 6.98 g of tetraethylorthosilicate (TEOS) [Sigma-Aldrich, 98% (wt/wt)] was then added and the mixture was stirred for 30 min. A separate solution was prepared by dissolving 0.094 g of tin (IV) chloride pentahydrate (SnCl$_4$.5H$_2$O) [Sigma-Aldrich, 98% (wt/wt)] in 1 g of water, and this solution was added dropwise to the first solution under stirring conditions. The resulting mixture was covered and stirred overnight to allow complete hydrolysis of the TEOS. The desired water ratio in the gel was obtained by complete evaporation of ethanol and some water. Next, 0.739 g of hydrofluoric acid (HF) solution [Sigma-Aldrich, 48% (wt/wt)] was added, resulting in a thick gel with a composition of SiO$_2$/0.01 SnCl$_4$/0.54 TEAOH/0.54 HF/6.75 H$_2$O. Finally, 0.6 g of a seed solution of dealuminated silica-based Beta crystals in water, prepared according to the method reported by Chang, et. al., "Rapid synthesis of Sn-Beta for the isomerization of cellulosic sugars. *RSC Adv* 2:10475 (2012), were added to the gel. The gel was transferred to a Teflon-lined stainless steel autoclave and heated at 140° C. under rotating conditions for 7 days. The solids were recovered by centrifugation, washed with water (3×) and acetone (1×), and dried at 100° C. overnight. The solid was calcined at 580° C. for 6 h to remove the organic content within the cystalline material.

Si-BEA was synthesized using essentially the same procedure, but without the addition of the SNnCl$_4$.

Synthesis of Zr-Beta: Zr-Beta molecular sieve was prepared as follows: 7.46 g of an aqueous tetraethylammonium hydroxide (TEAOH) solution [Sigma-Aldrich, 35% (wt/wt)] was diluted with 15 g of water. 6.98 g of tetraethylorthosilicate (TEOS) [Sigma-Aldrich, 98% (wt/wt)] was then added and the mixture was stirred for 30 min. A separate solution was prepared by diluting 0.123 g of zirconium (IV) propoxide [Sigma-Aldrich, 70% (wt/wt) in propanol] in 2 g of ethanol, and this solution was added dropwise to the first solution under stirring conditions. The resulting mixture was covered and stirred overnight to allow complete hydrolysis of the TEOS. The desired water ratio in the gel was obtained by complete evaporation of ethanol, propanol and some water. Next, 0.739 g of hydrofluoric acid (HF) solution [Sigma-Aldrich, 48% (wt/wt)] was added, resulting in a thick gel with a composition of SiO$_2$/0.01 ZrO$_2$/0.54 TEAOH/0.54 HF/6.75 H$_2$O. Finally, 0.6 g of a seed solution of dealuminated silica-based Beta crystals in water, prepared according to the method reported by Chang, et. al. was added to the gel. The gel was transferred to a Teflon-lined stainless steel autoclave and heated at 140° C. under rotating conditions for 4 days. The solids were recovered by centrifugation, washed with water (3×) and acetone (1×), and dried at 100° C. overnight. The solid was calcined at 580° C. for 6 h to remove the organic content within the cystalline material.

Synthesis of Ti-Beta: Ti-Beta molecular sieve was prepared as follows: 3.53 g of tetraethylammonium fluoride hydrate [Alfa Aesar, 97% (wt/wt)] was dissolved in 7 g of water. 7 g of tetraethylorthosilicate (TEOS) [Sigma-Aldrich, 98% (wt/wt)] was then added and the mixture was stirred for 30 min. A separate solution was prepared by diluting 0.123 g of titanium (IV) isopropoxide [Sigma-Aldrich, 99%] in 2 g of ethanol, and this solution was added dropwise to the first solution under stirring conditions. The resulting mixture was covered and stirred overnight to allow complete hydrolysis of the TEOS. The desired water ratio in the gel was obtained by complete evaporation of ethanol, isopropanol and some water, resulting in a gel with composition 1 $SiO_2$/0.013 $TiO_2$/0.55 TEAF/8.07 $H_2O$. Finally, 0.15 g of pure silica-based Beta seeds was added to the gel. The gel was transferred to a Teflon-lined stainless steel autoclave and heated at 140° C. under static conditions for 14 days. The solids were recovered by centrifugation, washed with water (3×) and acetone (1×), and dried at 373 K overnight. The solid was calcined at 580° C. for 6 h to remove the organic content within the cystalline material.

Synthesis of Sn-MCM-41: Sn-MCM-41 was prepared as follows: 1.98 g of hexadecyltrimethylammonium bromide (CTAB) [Sigma-Aldrich, 98% (wt/wt)] was dissolved in 10 g of water. Next, 3.15 g of tetramethylammonium hydroxide solution (TMAOH) [Sigma-Aldrich, 25% (wt/wt) in water] was added. A separate solution was prepared by diluting 0.06 g of tin (IV) chloride pentahydrate ($SnCl_4.5H_2O$) [Sigma-Aldrich, 98% (wt/wt)] in 2.14 g of water, and this solution was added dropwise to the first solution under stirring conditions. Finally, 2 g of fumed silica [Cab-O-Sil EH-5, 99.9% purity] was added, resulting in a thick gel with composition 1 $SiO_2$/0.005 $SnCl_4$/0.16 CTAB/0.26 TMAOH/24.3 $H_2O$. The homogeneous gel was transferred to a Teflon-lined stainless steel autoclave and heated at 140° C. under static conditions for 24 hours. The solids were recovered by centrifugation, washed with water (3×) and acetone (1×), and dried at 100° C. overnight. The solid was calcined at 580° C. for 6 h to remove the organic content within the ordered material.

Synthesis of Amorphous Sn—$SiO_2$ Material: The amorphous Sn—$SiO_2$ material was synthesized using a xerogel method and was prepared as follows: 6.989 g of tetraethylorthosilicate (TEOS) [Sigma-Aldrich, 98% (wt/wt)] was diluted with 8.682 g of water. 1.904 g of HCl solution (J. T. Baker, 0.1 N) was added and the resulting solution was stirred for 2 hours. Next, a second solution of 0.199 g of tin (IV) chloride pentahydrate ($SnCl_4.5H_2O$) [Sigma-Aldrich, 98% (wt/wt)] in 2 g of water was prepared and added dropwise to the first solution. After an additional hour of stirring, a tetrapropylammonium hydroxide (TPAOH) solution [Alfa Aesar, 40% (wt/wt)] was added dropwise until the gel hardened to a soft, colorless solid. The hardened gel was allowed to dry in a 100° C. oven overnight to produce the "as-made" xerogel solid. The resulting solid was calcined at 580° C. for 6 h.

Synthesis of Sn-MFI: Sn-MFI was prepared using a solid transformation of the "as-made" xerogel solid described above in the synthesis of the amorphous Sn—$SiO_2$ material: A tetrapropylammonium hydroxide (TPAOH) solution [20% (wt/wt)] was prepared by diluting a 40% (wt/wt) TPAOH solution (Alfa Aesar) with water. The 20% (wt/wt) TPAOH solution was added to the "as-made" xerogel solid (described above) in a ratio of 1.6 g TPAOH (20%):1 g xerogel solid, and this mixture was transferred to a Teflon-lined stainless steel autoclave and heated at 175° C. under static conditions for 24 hours. The solids were recovered by centrifugation, washed with water (3×) and acetone (1×), and dried at 373 K overnight. The solid was calcined at 580° C. for 6 h to remove the organic content within the cystalline material.

Ti-MFI was prepared by an analogous procedure. Zr-MFI was prepared in a procedure adapted by C. M. Lew, *Micro. Meso. Mat.*, 2012, 55-58

Example 1.2

Characterization of Catalytic Materials

Figure 3A:
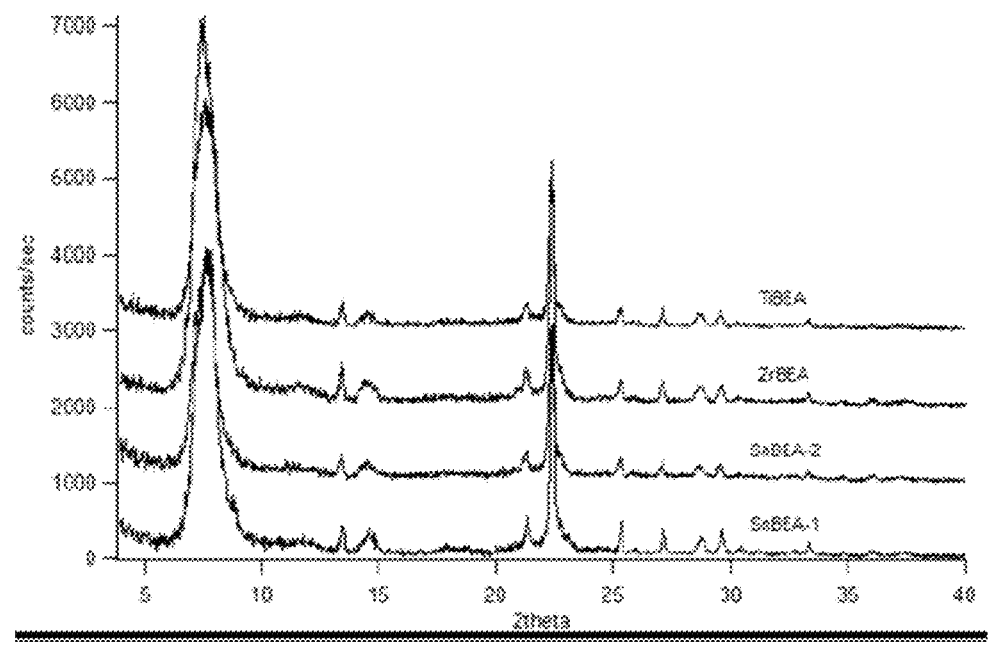
FIGS. 3A-C provides powder XRD patterns of catalytic materials, as described in Example 1.2.
Figure 3B:
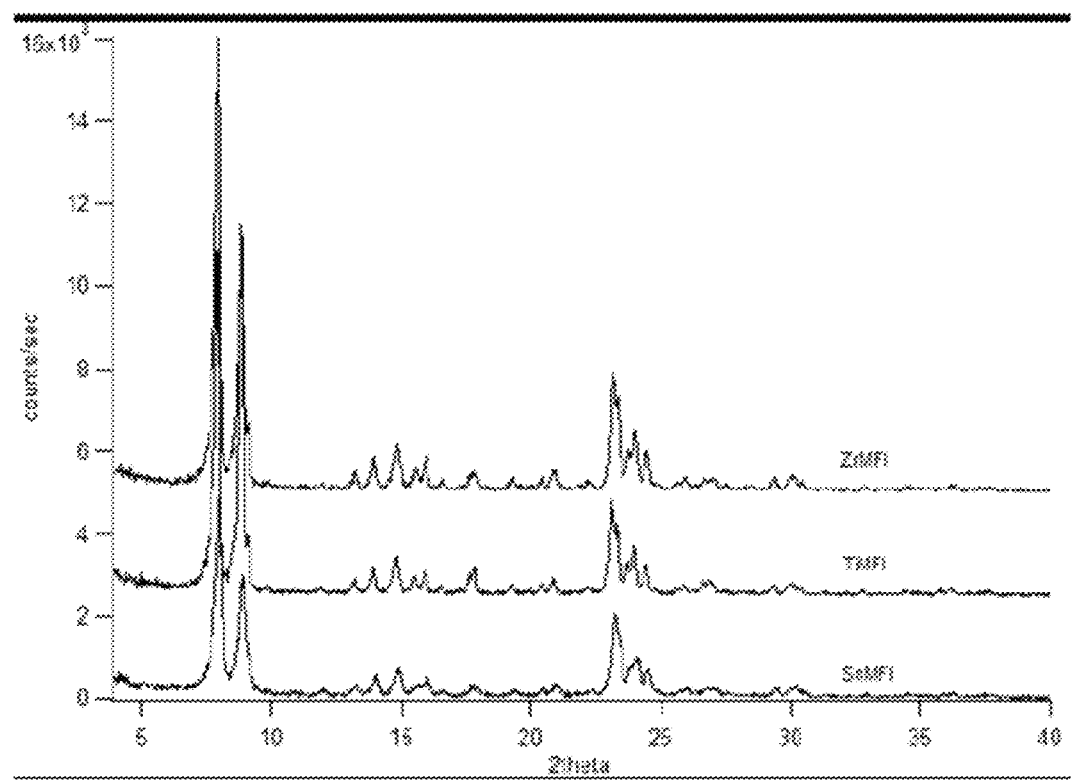
Figure 3C:
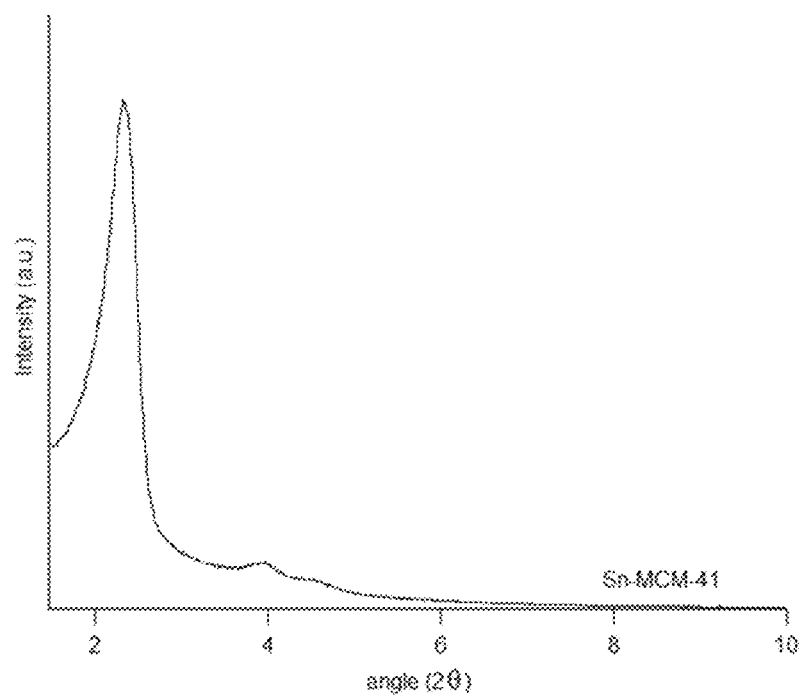

Powder X-ray diffraction (XRD) patterns were collected using a Rigaku Miniflex II diffractometer and Cu Kα radiation. Energy Dispersive X-ray Spectroscopy (EDS) measurements were recorded on a LEO 1550 VP FE SEM at an electron high tension (EHT) of 15 kV. Powder X-ray diffraction (XRD) confirmed that the Sn-Beta and Zr-Beta materials had the silica-based Beta topology and the absence of any bulk metal oxide phases. The XRD patterns are provided in the FIG. 3A-C. EDS results are provided in the Table 1.

TABLE 1

Energy Dispersive X-ray Spectroscopy (EDS) results for each material

| Material | Metal, M | Si/M |
|---|---|---|
| Sn-Beta | Sn | 106 |
| Zr-Beta | Zr | 185 |
| Ti-Beta | Ti | 93.1 |
| Sn-MCM-41 | Sn | 169 |
| Sn—$SiO_2$ | Sn | 57.1 |
| Sn-MFI | Sn | 92.6 |
| Ti-MFI | Ti | 79 |
| Zr-MFI | Zr | 163 |

Figure 4:
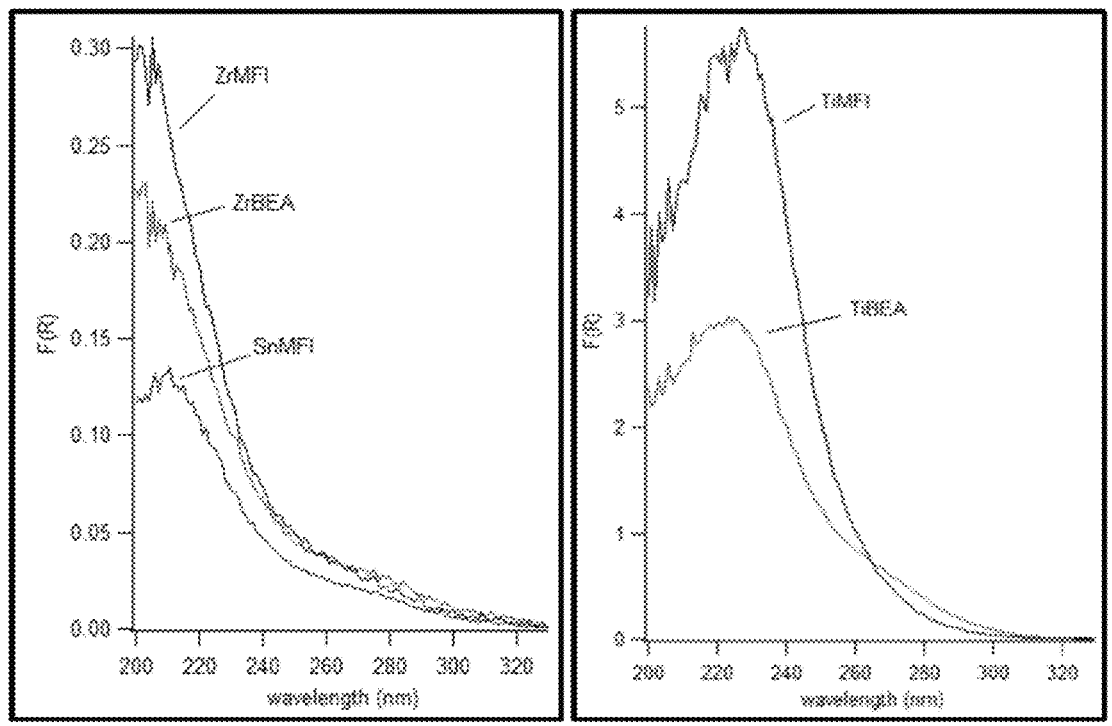
FIG. 4 provides diffuse reflectance UV spectra of materials used in this work, as described in Example 1.2.

Diffuse reflectance ultraviolet spectra shown in FIG. 4 were also taken for each of the calcined materials, except for the Sn-BEA samples. Each material shows a peak in the 200-220 nm region which is typically supportive evidence of the heteroatom tetrahedrally coordinated within the silica-based catalyst framework.

Example 1.3

Sources of Organic Precursors and Products

Methyl 4-(methoxymethyl)benzenecarboxylate (MMBC) was prepared from 4-(methoxymethyl)benzoic acid (Sigma-Aldrich) by esterification in methanol using HCl as catalyst. The reaction was conducted under reflux conditions for 2.5 hours. Following the reaction, water and ethyl acetate was added and the MMBC product was separated using liquid extraction into the ethyl acetate phase. The ethyl acetate was then removed by rotary evaporation to obtain the isolated MMBC product. The $^1$H NMR spectrum of the product was collected in $CDCl_3$, and the peak positions and integrated areas matched that of the reported $^1$H NMR spectrum for this molecule.

Other dienes and Diels-Alder-dehydration product standards were obtained commercially from sources shown in Table 2. The furans were used as-received.

TABLE 2

List of suppliers for dienes and Diels-Alder-dehydration product standards.

| Entry | Chemical | Supplier |
|---|---|---|
| 1 | 5-(hydroxymethyl)furoic acid | Matrix Scientific |
| 2 | 4-(hydroxymethyl)benzoic acid | Sigma-Aldrich |

TABLE 2-continued

List of suppliers for dienes and Diels-Alder-dehydration product standards.

| Entry | Chemical | Supplier |
|---|---|---|
| 3 | methyl 5-(methoxymethyl)furan-2-carboxylate | Enamine |
| 4 | methyl 4-(methoxymethyl)benzenecarboxylate | Prepared by esterification of entry 8[a] |
| 5 | methyl 5-(hydroxymethyl)furan-2-carboxylate | Matrix Scientific |
| 6 | methyl 4-(hydroxymethyl)benzenecarboxylate | Sigma-Aldrich |
| 7 | 5-(methoxymethyl)furoic acid | Matrix Scientific |
| 8 | 4-(methoxymethyl)benzoic acid | Sigma-Aldrich |
| 9 | 5-methyl-2-furoic acid | Sigma-Aldrich |
| 10 | p-toluic acid | Sigma-Aldrich |
| 11 | methyl 5-methyl-2-furoate | Sigma-Aldrich |
| 12 | methyl p-toluate | Sigma-Aldrich |
| 13 | 2,5-furandicarboxylic acid | Sigma-Aldrich |
| 14 | terephthalic acid | Sigma-Aldrich |
| 15 | 5-methylfurfural | Sigma-Aldrich |
| 16 | p-tolualdehyde | Sigma-Aldrich |
| 17 | 2,5-bis(hydroxymethyl)furan | Ark Pharm, Inc. |
| 18 | 1,4-benzenedimethanol | Sigma-Aldrich |
| 19 | 5-hydroxymethylfurfural | Sigma-Aldrich |
| 20 | 4-hydroxymethylbenzaldehyde | BOC Sciences |

Example 2

General Methods of Diels-Alder-Dehydration Reactions of Substituted Furans

Experiments were carried out in a 50 ml high pressure stainless steel batch reactor (Parr Series 4590) equipped with a magnetic stirrer and heater. The reactor setup allowed for ethylene gas (Matheson, 99.995% purity) or helium to be charged to the reactor. In a typical experiment, 100 mg of catalyst and 10 g of a 0.1 M diene solution in dioxane (Sigma-Aldrich, 99.8%) was loaded into the reactor. The magnetic stirrer was operated at 200 rpm and the head space of the reactor was purged with helium gas with a fill/vent cycle (10 times). Next, the reactor was pressurized to 37 bar (room temperature) with ethylene gas, the inlet valve was closed, and the reaction was performed in batch operation. The reactor was heated to 190° C. while the total pressure increased autogenously to 70 bar. At the end of the reaction time, the reactor was allowed to cool to room temperature and the reactor gases were vented. The product was then collected for analysis.

For each reaction, the starting diene solution and product solution were both analyzed by $^1$H NMR spectroscopy as follows: 0.2 g of each solution (the starting diene solution and product solution) was added to separate 1 g DMSO-$d_6$ solutions containing a known concentration of tetraethylsilane as an internal standard. The two mixtures were transferred through filtering pipettes into NMR tubes and the $^1$H NMR spectrums were collected at room temperature. By using the tetraethylsilane peak, the concentrations could be determined and conversions and yields were calculated. For example, the signals used for calculating the conversion of MMFC and the yield of MMBC: tetraethylsilane δ=0.49 ppm (q, 8H); MMFC δ=6.63 ppm (d, 1H) and δ=7.26 ppm (d, 1H); MMBC δ=7.46 ppm (d, 2H) and δ=7.95 ppm (d, 2H).

Example 3

Reversible Reaction Between Furan and Acrylic Acid

Example 3.1

Experimental Conditions

The reaction system used was a liquid-phase reaction conducted in a thick-walled glass reactor using a stir bar and a crimp-top seal. The reactor was charged with 3 grams of furan [Sigma Aldrich], 0.3 grams of acrylic acid [Sigma Aldrich], and catalyst (Sn-BEA, Zr-BEA, or T-BEA) was added to meet the target molar ratio of 360 acrylic acid:metal atoms. The reaction was carried out in a 50° C. water bath positioned on top of a stir plate. Samples (20 microliter aliquots) were taken over time using a microsyringe. The aliquots were diluted in CDCl$_3$ containing a known concentration of tetraethyl silane as an internal standard, transferred through a filter pipette into an NMR tube to remove the solid catalyst, and analyzed using quantitative $^1$H NMR.

Example 3.2

Results of Reversible Reaction Between Furan and Acrylic Acid

Figure 5:
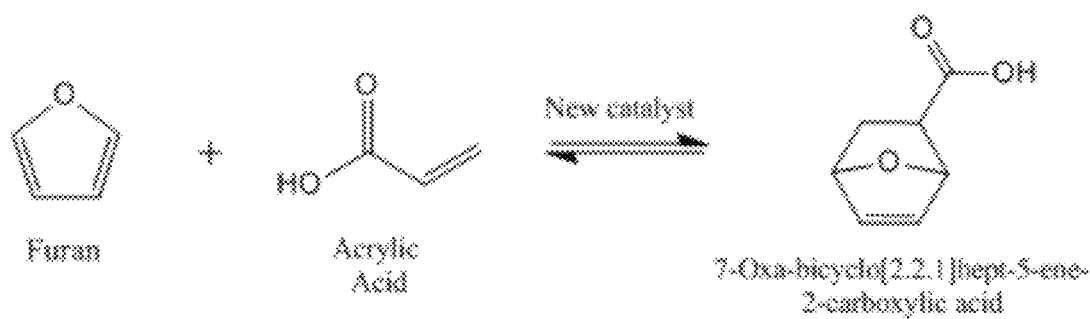
FIG. 5 shows an illustrative example of the reaction between furan and acrylic acid, as described in Example 3.

These experiments were done to demonstrate that the solid Diels-Alder reaction catalyst can also be used to perform the reversible Diels-Alder reaction (without the dehydrative aromatization step) between a furanic diene and a dienophile to produce the oxa-bicyclic heptene adduct in high selectivity. In particular, the reaction between furan and acrylic acid to produce 7-oxa-bicyclo[2.2.1]hept-5-ene-2-carboxylic acid. While these experiments were done with acrylic acid, it is expected that other substituted dienophiles may also be used with these catalytic conditions. The reaction scheme is shown in FIG. 5 and is known to be catalyzed by homogeneous Lewis acids. Table 3 summarizes experimental conditions and results for the Diels-Alder reaction between furan and acrylic acid using the silica-based Lewis acid *BEA structure catalysts. These data show that Sn-BEA and Zr-BEA were active catalysts for this reaction when compared to the control Si-BEA material, with acrylic acid conversions of about 30% and greater than about 95% selectivity to the Diels-Alder adduct after several hours of reaction time. The reactions became equilibrium limited at long reaction times since equilibrium conversion of acrylic acid was about 40% under these reaction conditions. See FIG. 6.

TABLE 3

Experimental conditions and results for Diels-Alder reaction between acrylic acid and furan using Lewis acid *BEA type catalysts

| Acrylic Acid, M | Catalyst | Temp, ° C. | Reaction time, min | Conversion | Selectivity |
|---|---|---|---|---|---|
| 1.3 | Sn-BEA | 50 | 150 | 30% | >95% |
| 1.3 | Zr-BEA | 50 | 180 | 29% | >95% |
| 1.3 | Ti-BEA | 50 | 150 | 8% | >95% |
| 1.3 | Si-BEA | 50 | 150 | 7% | >95% |

Example 4

Initial Screening Reactions of Diels-Alder/Aromatization Reactions

Example 4.1

Converting DMF to p-Xylene

Initial experiments converting dimethyl furan (DMF) to para-xylene showed good results using Sn-BEA and Zr-BEA catalysts, even in hexane solvent (Table 4). Note that a Brønsted acid-containing catalyst (H-BEA) was able to perform the conversion to p-xylene when the furan contains non-oxygenated substituents (i.e., methyl groups).

Example 4.2

Four additional examples of the reactions of substituted furans are shown in FIG. 7. These are the Diels-Alder/aromatization reactions between ethylene and furoic acid, 2-acetyl-5-methylfuran, 5-methyl-2-furoic acid, and methyl 5-methyl-2-furoate to produce benzoic acid, 4-methylacetophenone, p-toluic acid, and methyl p-toluate, respectively. Each of these furanic dienes can be obtained from known methods starting from furfural, and furfural can be produced from xylose analogous to HMF production from glucose.

Table 5 summarizes experiment conditions and results for these four new Diels-Alder/aromatization reactions. When methy 5-methyl-2-furoate is used as the diene, nearly 100% selectivity to the methyl p-toluate product can be achieved. The last line shows an experiment in which pure silica *BEA catalyst was used instead of Sn-BEA and the result was no conversion, therefore showing that a Lewis acid site in the silica catalyst such as tin is required for the Diels-Alder/aromatization reaction to occur.

TABLE 4

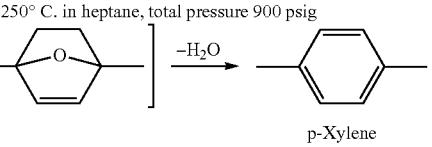

Reactions run 6 hours at 250° C. in heptane, total pressure 900 psig

| Catalyst | Catalyst, mg | DMF Conversion | p-Xylene Yield |
|---|---|---|---|
| H-BEA (Si/Al = 13.5) | 100 | 43% | 30% |
| Sn-BEA (Si/Sn = 107) | 154 | 45% | 21% |
| Sn—Al-BEA (Si/Sn = 115, Si/Al = 90) | 195 | 33% | 22% |
| Zr-BEA (Si/Zr = 182) | 70 | 30% | 6% |
| No catalyst | 0 | 1% | 1% |

TABLE 5

Experimental conditions and results for Diels-Alder/Aromatization reactions shown in FIG. 7. In each case, reactant concentration was 0.4M in 1,4-dioxane; reaction temperature was 225° C.; total pressure was 1000 psig. For FA to BA conversion, reactant concentration was 0.2M

| Reactant | Product | Catalyst (mg) | Time, hr | Conversion | Yield |
|---|---|---|---|---|---|
| Furoic acid (FA) | Benzoic acid (BA) | Sn-BEA (102) | 6 | 55% | 2% |
| 2-acetyl-5-methyl furan (AMF) | 4-methylacetophenone (MAP) | Sn-BEA (200) | 6 | 4-Methylacetophenone was confirmed product in ¹H NMR spectrum, but conversion and yield not quantified | |

TABLE 5-continued

Experimental conditions and results for Diels-Alder/Aromatization reactions shown in FIG. 7. In each case, reactant concentration was 0.4M in 1,4-dioxane; reaction temperature was 225° C.; total pressure was 1000 psig. For FA to BA conversion, reactant concentration was 0.2M

| Reactant | Product | Catalyst (mg) | Time, hr | Conversion | Yield |
|---|---|---|---|---|---|
| 5-methyl-2-furoic acid (MFA) | p-toluic acid (TA) | Sn-BEA (200) | 6 | 82% | 14% |
| methyl-5-methyl-2-furoate (MMF) | methyl p-toluate (MPT) | Sn-BEA (200) | 6 | 13% | 13% |
| | | Sn-MCM-41 (200) | 6 | 12% | 12% |
| | | Sn—SiO$_2$ (200) | 6 | 11% | 11% |
| | | Si-BEA (200) | 6 | 0% | 0% |

The Diels-Alder/aromatization catalysts Sn-MCM-41 and Sn—SiO$_2$ are pure silica MCM-41 containing tin and amorphous silica containing tin, respectively. Si-BEA is a pure silica-based catalyst structure. Like the experiments summarized in Table 5, the solvent used for these reactions was dioxane. The reactions are conducted in a batch reactor pressurized with ethylene gas. Conversions and yields have been determined using quantitative $^1$H NMR with an internal standard.

This is the first report for each of these reactions in Table P1-2. Therefore, this invention allows for completely novel routes to producing these chemical products, and likely others, from biomass-derived furans such as furfural and HMF as shown in FIG. 8.

Example 4.3

Attempted Conversion of HMF to HMB

Initial screening experiments, testing a range of various solvents, catalysts (heterogeneous and homogeneous), reaction temperatures, pressures and times, and 5-hydroxy-2-furfural (HMF) concentrations, failed to identify a system in which 4-hydroxymethyl benzaldehyde (HMB) formed. Reactions generally results in significant carbon deposition or coking of the catalysts.

Example 4.4

Converting BHMF to BHMB

Preliminary experiments converting 2,5-bishydroxymethyl furan (BHMF) to 1,4-bishydroxymethyl benzene (BHMB) showed encouraging results using Sn-BEA (Table 6). Yields were not quantified, but product was identified in $^1$H NMR spectra and gas chromatographs. At temperatures above 150° C., the BHMF decomposed, mainly forming furan and formaldehyde through a dehydroxymethylation reaction.

TABLE 6

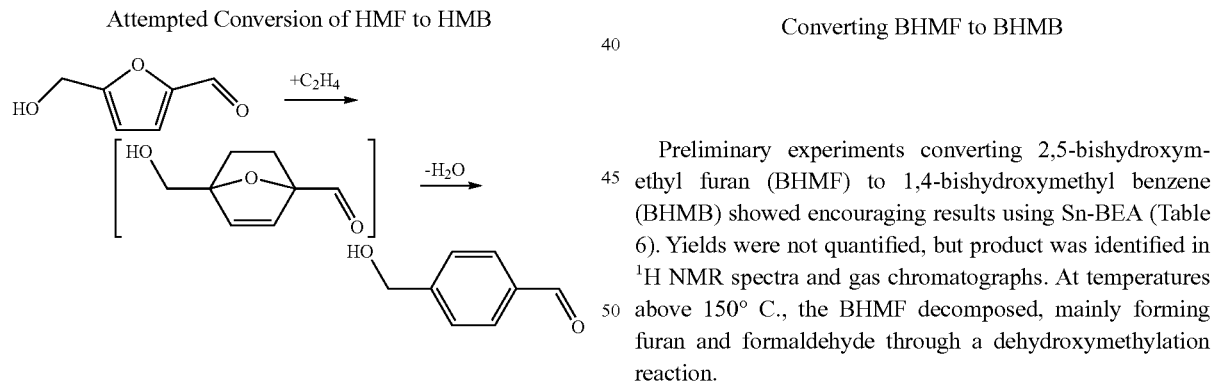

| Catalyst | BHMF (M; in dioxane) | Temp, ° C. | Time, hrs | Observations |
|---|---|---|---|---|
| Sn-BEA | 0.1 | 250 | 16 | Dark/black liquid and catalyst; significant dehydroxymethylation |
| Sn-BEA | 0.1 | 150 | 1 | Low BHMF conversion; some dehydroxymethylation |

TABLE 6-continued

| Catalyst | BHMF (M; in dioxane) | Temp, °C. | Time, hrs | Observations |
|---|---|---|---|---|
| Sn-BEA | 0.1 | 150 | 6 | Some dehydroxymethylation; low yields of BHMB |
| Sn-BEA | 0.25 | 150 | 42 | BHMF completely converted; low yields of BHMB |

Example 4.5

Converting FDCA to PTA

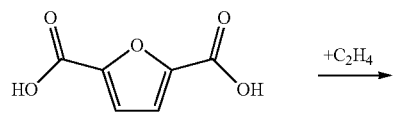

Preliminary experiments with 2,5-furan dicarboxylic acid (FDCA) resulted in low, but measurable yields of terephthalic acid (PTA) (ca. 1-3 mole %; reaction conditions were 225° C., 1000 psig ethylene, 4-16 hrs, in dioxane). Degradation products, which otherwise resulted in brown or black product solution, were avoided using the Lewis-acid containing pure silica BEA molecular sieves. Homogeneous Lewis acid, Sc(OTf)$_3$, and solid Brønsted acid, H-BEA, did not produce any PTA, though significant FDCA degradation was observed as apparent from the brown or black product solution. Additional experiments conducted under the conditions described in U.S. Patent Application Publication No. 2009/0124829, filed Nov. 14, 2007 yielded no measurable PTA yield as determined by $^1$H NMR analysis of the products.

TABLE 7

Experiment conditions and results for Diels-Alder/Aromatization reactions between FDCA and ethylene, and DMFC and ethylene.

| Reactant | Product | Catalyst | Catalyst amount (mg) | Conversion | Yield |
|---|---|---|---|---|---|
| FDCA | PTA | Sn-BEA | 200 | N/A | 1-3% |
| | | Zr-BEA | 122 | N/A | 1-3% |
| | | Ti-BEA | 200 | N/A | 1-3% |
| DMFC | DMT | Sn-BEA | 169 | 43% | 0.4% |

All experiments conducted in 1,4-dioxane, 1M in reactant, 225° C., 1000 psig for 16 hrs, except DMFC to DMT conversion conducted with 0.28M reactant, 300° C., 850 psig for 6 hrs.

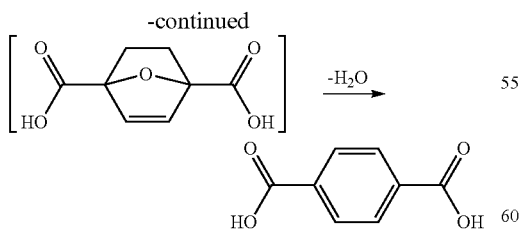

The Diels-Alder/aromatization catalysts Sn-BEA, Zr-BEA, and Ti-BEA are pure silica molecular sieves with the *BEA framework containing framework substituted tin, zirconium, and titanium, respectively. The solvent used for these reactions was dioxane. The reactions are conducted in a batch reactor pressurized with ethylene gas. Conversions and yields have been determined using quantitative $^1$H NMR with an internal standard.

Two specific examples of the present methods are shown in FIG. 8. These are the conversion of 2,5-furandicarboxylic acid (FDCA) and ethylene to terephthalic acid (PTA) and water through the Diels-Alder/aromatization reaction, and the conversion of methyl-5-methoxymethyl-2-furancarboxylate (MMFC) and ethylene to methyl-4-methoxymethyl benzenecarboxylate (MMBC) and water. MMBC can then be hydrolyzed back to the alcohol and acid form, which in turn is oxidized to terephthalic acid. Both FDCA and MMF can be obtained from glucose-derived HMF through known methods.

Example 4.6

Converting HMFA to HMBA

A series of experiments were conducted to test the variables related to the conversion of 5-hydroxymethyl-2-furoic acid (HMFA) to 4-hydroxymethylbenzoic acid (HMBA). This transformation is a key intermediate step in the transformation of hydroxymethyl furfural (HMF) to (purified) terephthalic acid (PTA), according to:

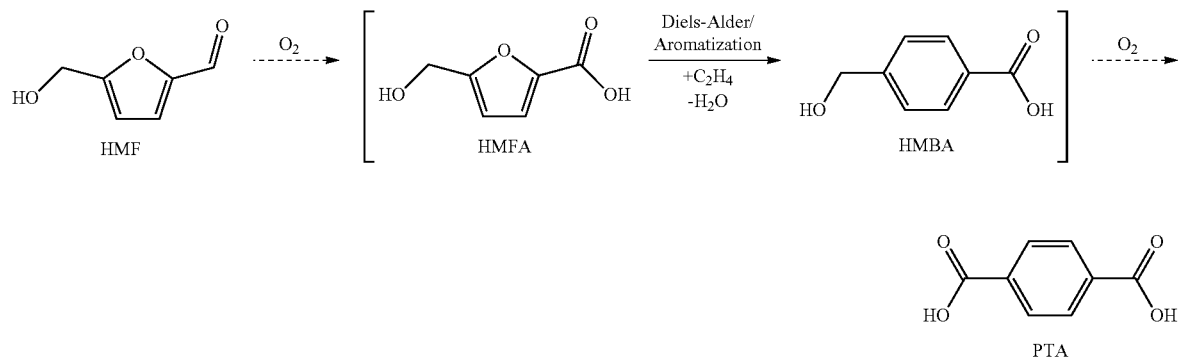

The results are shown in Tables 8 and FIG. 9. Reaction conditions for FIG. 9 were 1000 psig ethylene at 190° C., 10 g of a 100 mM dioxane solution of HFMA, with 100 mg Sn-Beta catalyst.

TABLE 8

All reactions were run at 850-1000 psig total pressure, 190° C., 10 g of a 100 mM HFMA solution, 100 mg catalyst.

| Entry | Catalyst | Solvent | Time (hr) | HMFA Converson (%) | HMBA Yield (%) | HMBA Selectivity (%) |
|---|---|---|---|---|---|---|
| 1 | Sn-Beta | dioxane | 0.5 | 18 | 4 | 22 |
| 2 | Sn-Beta | dioxane | 2 | 36 | 11 | 31 |
| 3 | Sn-Beta | dioxane | 4 | 57 | 15 | 26 |
| 4 | Sn-Beta | dioxane | 6 | 61 | 19 | 31 |
| 5 | Sn-Beta | dioxane | 12 | 76 | 21 | 28 |
| 6 | Sn-Beta | dioxane/water 1:1 v/v | 0.5 | 94 | 0 | 0 |
| 7 | Sn-Beta | THF+ | 0.5 | 35 | 2 | 6 |
| 8 | Zr-Beta | dioxane | 6 | 87 | 9 | 10 |
| 9 | None | dioxane | 2 | 5 | 0 | 0 |
| 10 | None | dioxane | 6 | 21 | 0 | 0 |
| 11 | Si-Beta | dioxane | 2 | 20 | 0 | 0 |
| 12 | Si-Beta | dioxane | 6 | 56 | <1 | <1 |
| 13 | Si-MFI | dioxane | 2 | 25 | 0 | 0 |

+9 g of solution used

Example 4.7

Converting MMFA to MMBA

A series of experiments were conducted in dioxane at 1000 psig total pressure ethylene to test the variables related to the conversion of 5-(methoxymethyl)-2-furoic acid (MMFA) to 4-(methoxymethyl)benzoic acid (MMBA). The results are shown in Table 9.

TABLE 9

Reactions were run in dioxane at 1000 psig ethylene total pressure.

(MMFA) → Diels-Alder/Aromatization, +C₂H₄, −H₂O → (MMBA)

| Entry | [MMFA], mM | Catalyst (mg) | Temp, °C. | Time, hr | MMFA Conversion | MMBA Yield | MMBA Selectivity |
|---|---|---|---|---|---|---|---|
| 1 | 100 | Sn-BEA (100) | 190 | 2 | 36% | 6% | 17% |
| 2 | 100 | Sn-BEA (100) | 190 | 6 | 52% | 9% | 17% |

Example 4.8

Converting HMFC to HMBC

An experiment was conducted in dioxane at 1000 psig total pressure ethylene related to the conversion of methyl-(5-hydroxymethyl-furan-2-carboxylate (HMFC) to methyl 4-hydroxymethylbenzenecarboxylate (HMBC). The results are shown in Table 10.

TABLE 10

Reactions was run in dioxane at 1000 psig ethylene total pressure.

(HMFC) → Diels-Alder/Aromatization, +C₂H₄, −H₂O → HMBC

| Entry | [HMFC], mM | Catalyst (mg) | Temp, °C. | Time, hr | HMFC Conversion | HMBC Yield | HMBC Selectivity |
|---|---|---|---|---|---|---|---|
| 1 | 100 | Sn-BEA (100) | 190 | 6 | 12% | 5% | 42% |

Example 4.9

Converting MMFC to MMBC

A series of preliminary experiments were conducted to test the variables related to the conversion of methyl-5-methoxymethyl-2-furancarboxylate (MMFC) to methyl-(4-methoxymethyl)benzenecarboxylate (MMBC). The results are shown in Tables 11A-C.

TABLE 11A

All reactions were run in dioxane at 1000 psig ethylene total pressure.

(MMFC) → Diels-Alder/Aromatization, + C₂H₄, −H₂O → (MMBC)

| Entry | [MMFC], mM | Catalyst (mg) | Temp, °C. | Time, hr | MMFC Conversion | MMBC Yield | MMBC Selectivity |
|---|---|---|---|---|---|---|---|
| 1 | 100 | Sn-BEA (100) | 190 | 0.5 | 11% | 6% | 55% |
| 2 | 100 | Sn-BEA (100) | 190 | 2 | 28% | 13% | 46% |
| 3 | 100 | Sn-BEA (100) | 190 | 4 | 46% | 20% | 43% |

TABLE 11A-continued

All reactions were run in dioxane at 1000 psig ethylene total pressure.

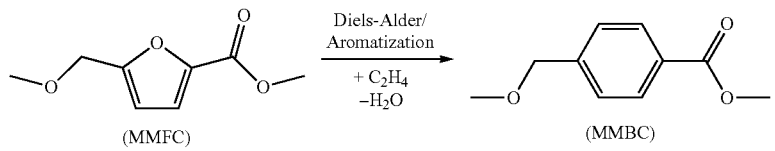

| Entry | [MMFC], mM | Catalyst (mg) | Temp, °C. | Time, hr | MMFC Conversion | MMBC Yield | MMBC Selectivity |
|---|---|---|---|---|---|---|---|
| 4 | 100 | Sn-BEA (100) | 190 | 6 | 50% | 24% | 48% |
| 5 | 100 | Sn-BEA (100) | 190 | 12 | 78% | 23% | 29% |
| 6 | 60 | Sn-BEA (100) | 145 | 6 | 9% | 4% | 44% |
| 7 | 70 | Sn-BEA (400) | 175 | 6 | 37% | 17% | 46% |
| 8 | 110 | Sn-BEA (100) | 175 | 4 | 30% | 10% | 33% |
| 9 | 140 | Sn-BEA (50) | 190 | 6 | 16% | 8% | 50% |
| 10 | 410 | Sn-BEA (50) | 190 | 6 | 33% | 12% | 36% |
| 11 | 100 | Zr-BEA (100) | 190 | 2 | 15% | 11% | 73% |
| 12 | 100 | Zr-BEA (100) | 190 | 4 | 22% | 16% | 73% |
| 13 | 100 | Zr-BEA (100) | 190 | 6 | 26% | 21% | 81% |
| 14 | 100 | Zr-BEA (100) | 190 | 12 | 42% | 32% | 76% |

<sup>a</sup> in dioxane/hexane (1:1)

TABLE 11B

Additional Results for the Diels-Alder-dehydration of MMFC and ethylene

| Entry | Catalyst | Solvent | Time (hr) | Temperature (°C.) | MMFC Conversion (%) | MMBC Yield (%) | MMBC Selectivity (%) |
|---|---|---|---|---|---|---|---|
| 1 | None | dioxane | 6 | 190 | 1 | 0 | 0 |
| 2 | Sn-Beta | dioxane | 2 | 190 | 28 | 13 | 46 |
| 3 | Sn-Beta | dioxane/hexane 1:1 v/v | 2 | 190 | 33 | 12 | 36 |
| 4 | Sn-Beta | dioxane | 2 | 210 | 44 | 13 | 30 |
| 5 | Sn-Beta | dioxane | 6 | 190 | 50 | 24 | 48 |
| 6 | Zr-Beta | dioxane | 6 | 190 | 26 | 21 | 81 |
| 7 | Ti-Beta | dioxane | 12 | 190 | 2 | 1 | 50 |
| 8 | Sn-MCM-41 | dioxane | 6 | 190 | 5 | 1 | 20 |
| 9 | Sn—SiO$_2$ (amorphous) | dioxane | 6 | 190 | 16 | 2 | 13 |
| 10 | Sn-MFI | dioxane | 6 | 190 | 9 | 1 | 11 |
| 11 | H—Al-Beta (Si/Al = 13.5) | dioxane | 6 | 190 | 100 | 2 | 2 |

Experiments were carried out with 1000 psig of ethylene gas and reactor was charged with 10 g of a 0.1M solution of MMFC and 100 mg of catalyst. Powder XRD patterns are provided in FIG. 3A-C, and the silicon/metal ratios for solids are provided in Table 1.

TABLE 11C

Additional Results for the Diels-Alder-dehydration of MMFC and ethylene

| Entry | Catalyst | Catalyst Si/M ratio | Furan:M ratio | MMFC Conversion (%) | MMBC Yield (%) | MMBC Selectivity (%) |
|---|---|---|---|---|---|---|
| 1 | None | — | — | 1 | 0 | 0 |
| 2 | Si-Beta | — | — | 2 | 0 | 0 |
| 3 | Zr-Beta | 221 | 126 | 23 | 18 | 78 |
| 4 | Zr-Beta | 185 | 106 | 26 | 21 | 81 |
| 5 | Zr-Beta | 152 | 87 | 26 | 18 | 69 |
| 6 | Zr-Beta | 116 | 66 | 34 | 29 | 85 |
| 7 | Zr-Beta* | 116 | 22 | 51 | 32 | 63 |

TABLE 11C-continued

Additional Results for the Diels-Alder-dehydration of MMFC and ethylene

| Entry | Catalyst | Catalyst Si/M ratio | Furan:M ratio | MMFC Conversion (%) | MMBC Yield (%) | MMBC Selectivity (%) |
|---|---|---|---|---|---|---|
| 8 | Sn-Beta | 106 | 61 | 50 | 24 | 48 |

Experiments were carried out with 1000 pig of ethylene gas at 190° C. for 6 hrs. Reactor was charged with 10 g of a 0.1M solution of MMFC and 100 mg of catalyst.
*300 mg catalyst used The performances of other catalytic materials were compared to Sn-Beta (Table 11B, entries 5-11). The type of Lewis acid metal center was varied (entries 6 & 7), and it was found that pure-silica Beta molecular sieves with $Zr^{4+}$ centers (Zr-Beta) were more selective catalysts for producing the Diels-Alder-dehydration product, MMBC, than Sn-Beta. Zr-Beta was 81% selective for MMBC at 26% MMFC conversion. $Ti^{4+}$ centers in Beta (Ti-Beta) were found to be much less active than $Sn^{4+}$ and $Zr^{4+}$. The spatial environment around the $Sn^{4+}$ was varied by preparing $Sn^{4+}$ containing mesoporous silica (MCM-41) and $Sn^{4+}$ containing amorphous silica (entries 8 & 9, respectively). Both materials produced lower yields and lower selectivities than Sn-Beta, suggesting that confinement effects within the microporous Beta framework are playing an important role in the selective formation of the Diels-Alder-dehydration product. Smaller micropore size was tested with a pure-silica medium pore molecular sieve (having the MFI topology) containing $Sn^{4+}$ (entry 10), and only a small amount of MMBC was formed. A commercial, calcined Al-Beta sample (Tosoh, Si/Al=13.5) was tested (entry 11), and complete conversion of MMFC with only 2% yield of MMBC was observed. Significant humins formation was apparent by the dark product solution and black solids obtained after reaction. Al-Beta contains a high concentration of Brønsted acid sites that catalyze many undesired side reactions (humins formation) involving the oxygenated functional groups of the furan, and therefore resulted in poor selectivities.

The MMFC conversion and MMBC yield as a function of reaction time using both Sn-Beta and Zr-Beta as catalysts are shown in FIG. 10. Both catalysts give similar MMBC yield profiles, producing 21-24% MMBC yield after 6 hours, but it is apparent from the MMFC conversion profiles that MMFC reacts faster on Sn-Beta relative to Zr-Beta. This may be in part explained by the higher amount of Sn in the Sn-Beta material compared to Zr in the Zr-Beta; energy dispersive X-ray spectroscopy (EDS) measurements show a Si/Sn ratio of 106 for the Sn-Beta catalyst while the Si/Zr ratio is 185 for the Zr-Beta catalyst. Fewer side reactions occur with the Zr-Beta catalyst, resulting in selectivities to the Diels-Alder-dehydration product of over 70%, compared to the _50% selectivities when using Sn-Beta.

Example 5

Overview of Diels-Alder-Dehydration Reactions of Substituted Furans

Several oxygenated furans were contacted with high pressure ethylene to screen for activity in the Diels-Alder-dehydration reaction using Sn-Beta as a catalyst. The results shown in Table 12 summarize the furans used in this aspect of the study and their relative reactivities. All experiments were carried out with 70 bar of ethylene gas at 190° C. for 6 hours; in each case, the reactor was charged with 10 g of a 0.1 M diene solution in dioxane and 100 mg of Sn-Beta catalysts, as prepared in Example 1.1.1.

Table 12, entries 5, 6, 8, and 9 are furans that are not readily obtained from HMF by oxidation steps only, but were included in the study to assist in the understanding of the effects of different functional groups on reactivity. Dioxane was found to be the preferred solvent, and data reported in Table 12 were obtained using this solvent.

TABLE 12

Results for the Diels-Alder/dehydration of oxygenated furans with ethylene

| Entry | Diene | Product | % conversion (diene) | % yield (product) | % selectivity† (product) |
|---|---|---|---|---|---|
| 1 | [structure: HO-furan-COOH] | [structure: HO-CH2-C6H4-COOH] | 61 | 19 | 31 |
| 2 | [structure: methoxymethyl-furan-COOMe] | [structure: MeO-CH2-C6H4-COOMe] | 50 | 24 | 48 |
| 3 | [structure: HO-CH2-furan-COOMe] | [structure: HO-CH2-C6H4-COOMe] | 12 | 5 | 42 |

TABLE 12-continued

Results for the Diels-Alder/dehydration of oxygenated furans with ethylene

| Entry | Diene | Product | % conversion (diene) | % yield (product) | % selectivity† (product) |
|---|---|---|---|---|---|
| 4 | 5-(methoxymethyl)furan-2-carboxylic acid | 4-(methoxymethyl)benzoic acid | 52 | 9 | 17 |
| 5 | 5-methylfuran-2-carboxylic acid | 4-methylbenzoic acid (p-toluic acid) | 45 | 12 | 27 |
| 6 | methyl 5-methylfuran-2-carboxylate | methyl 4-methylbenzoate (methyl p-toluate) | 12 | 12 | 100 |
| 7 | FDCA (furan-2,5-dicarboxylic acid) | terephthalic acid (PTA) | 0* | 0 | 0 |
| 8 | 5-methylfurfural | 4-methylbenzaldehyde | 2 | 0 | 0 |
| 9 | 2,5-bis(hydroxymethyl)furan | 1,4-bis(hydroxymethyl)benzene | 100 | <1 | <1 |
| 10 | 5-(hydroxymethyl)furfural (HMF) | 4-(hydroxymethyl)benzaldehyde | 16 | 0 | 0 |

†Selectivity defined as yield (product)/conversion (diene).
*The diene, FDCA, was mostly insoluble in dioxane at room temperature; the 0.1M solution was prepared as if all the FDCA were dissolved. Due to the insoluble nature of FDCA, concentrations (and therefore, conversions) were difficult to accurately measure with the method used. No PTA was produced per $^1$H NMR analysis.

The HMF oxidation product, HMFA (entry 1), is shown to be active in the Diels-Alder-dehydration reaction with ethylene to produce 4-(hydroxymethyl)benzoic acid (HMBA) with 31% selectivity at 61% HMFA conversion using the Sn-Beta catalyst. By protecting the hydroxymethyl and acid groups of HMFA with an alcohol (i.e., methanol) to produce the corresponding ether and ester groups, a 48% selectivity to the desired product at 50% furan conversion was achieved (entry 2). Each of the HMFA functionalities were protected with methanol independently (entries 3 & 4). When the acid function was protected the selectivity increased relative to the HMFA case along with a significant decrease in conversion, but when the hydroxymethyl function was protected the selectivity decreased along with a decrease in conversion. By using methanol to protect both functionalities, the highest yield (24%) of the Diels-Alder-dehydration product was obtained using the current Sn-Beta catalyst.

Substituting the hydroxymethyl group at the 5-position with a methyl (entries 5 & 6) produced an interesting result. When the acid function remained the selectivity to p-toluic acid was only 27%. When the acid was converted to the ester functionality an increase in selectivity was expected and, indeed, nearly 100% selectivity to methyl p-toluate was obtained at diene conversions of 12%. The 100% selectivity obtained for entry 6 suggests that only the carboxylic acid, hydroxymethyl, and methoxymethyl groups in entries 1-5 are resulting in side reactions, and the presence of the carboxylate ester group alone does not cause any side reactions.

The Diels-Alder-dehydration reaction of the fully oxidized HMF, FDCA, was investigated (entry 7), and FDCA was found to be generally unreactive. PTA yields of only $_{about}$ 2% could be obtained by using higher temperatures (225-250° C.) and longer times (10-16 hours). It is noteworthy that the product solution showed little sign visually (and also by $^1$H NMR) of any side or degradation reactions of the FDCA reactant, or of "coking" of the Sn-Beta catalyst; even after a reaction held at 225° C. for 14 hours, the catalyst and undissolved FDCA remained nearly white and the dioxane solution remained nearly colorless. We conclude that the strong deactivating effects of the two carboxyl groups rendered the Diels-Alder step with ethylene too slow for practical application, so no further testing was performed.

Entries 8-10 are furans that are without a carboxylic acid or carboxylate ester functionality, and results from these experiments showed no measurable yields of the Diels-Alder-dehydration products. Numerous additional attempts using these furans at various reaction conditions typically resulted in significant dark black humins formation, and rapid coking of the catalyst presumably prevented any formation of the desired product. Clearly, the presence of a single carboxylic acid or carboxylate ester function seems to be playing a critical role in the ability of oxygenated furans to selectively react with ethylene in the Diels-Alder-dehydration reaction in the presence of Sn-Beta.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A process comprising contacting a compound of Formula (1):

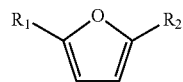
(1)

with a compound of Formula (2):

(2)

in a non-aqueous solvent in the presence of a solid, silica-based Lewis acid catalyst that is essentially devoid of strong Brønsted acid character;
under conditions sufficient to produce a compound of Formula (3) or Formula (4) or both:

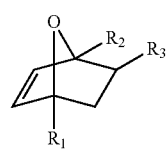
(3)

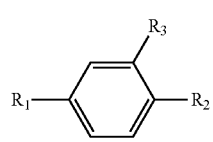
(4)

wherein $R_1$ and $R_2$ are each independently H, alkyl, or an oxygenated functional group, wherein at least one of $R_1$ or $R_2$ is the oxygenated functional group;
wherein $R_3$ is H, alkyl, or an oxygenated functional group;
wherein said oxygenated functional group is an acetal, aldehyde, protected aldehyde, acyl, protected acyl, hydroxycarbonyl, alkoxycarbonyl, hydroxymethyl or alkoxymethyl.

2. The process of claim 1, wherein $R_3$ is hydrogen.

3. The process of claim 1, wherein $R_1$ and $R_2$ are each independently an oxygenated functional group.

4. The process of claim 1, wherein the compound of Formula (1) is

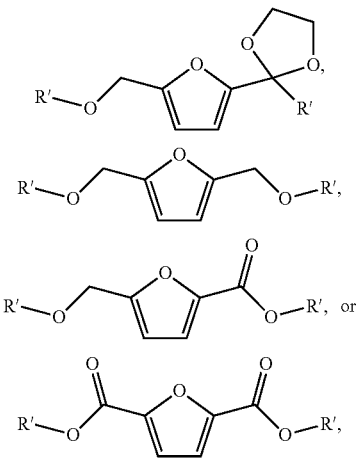

wherein R' is independently H or alkyl, or the compound of Formula

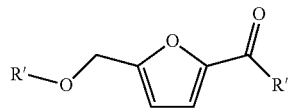

wherein R' is alkyl.

5. The process of claim 4, wherein the compound of Formula (1) is

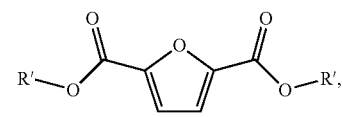

and the conditions sufficient to produce a compound of Formula (4) that is:

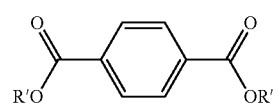

where R' are each independently H or alkyl.

6. The process of claim 4, wherein the compound of Formula (1) is

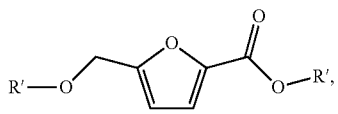

and the conditions sufficient to produce the compound of Formula (4) that is:

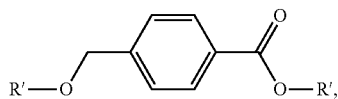

wherein R' are each independently H or alkyl.

7. The process of claim 1, wherein the compound of Formula (1) is

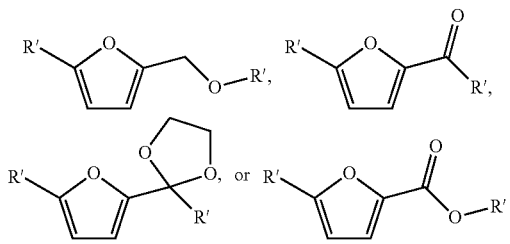

wherein R' is H or alkyl.

8. The process of claim 1, where $R_1$ and $R_2$ are each independently an acetal, aldehyde, alkoxycarbonyl, hydroxycarbonyl, hydroxymethyl, or alkoxymethyl; and $R_3$ is hydrogen, said process further comprising oxidizing the compound of Formula (4) under conditions sufficient to form terephthalic acid or an diester thereof.

9. The process of claim 1, wherein the solid silica-based Lewis-acid catalyst is a molecular sieve.

10. The process of claim 1, wherein the solid silica-based Lewis-acid catalyst comprises a microporous material.

11. The process of claim 1, wherein the solid silica-based Lewis-acid catalyst comprises a mesoporous material.

12. The process of claim 1, wherein the solid silica-based Lewis-acid catalyst is a silica-based molecular sieve having a 10-membered ring topology.

13. The process of claim 1, wherein the solid silica-based Lewis-acid catalyst is a silica-based molecular sieve having a *BEA topology.

14. The process of claim 1, wherein the solid silica-based Lewis-acid catalyst comprises Ge, Hf, Nb, Sn, Ta, Ti, Zr, or a combination thereof.

15. The process of claim 14, wherein the solid silica-based Lewis-acid catalyst comprises Sn, Ti, Zr, or a combination thereof.

16. The process of claim 15, wherein the solid silica-based Lewis-acid catalyst comprises Sn, Ti, Zr, or the combination thereof, and the Sn, Ti, Zr, or combination thereof is tetrahedrally coordinated within the solid silica-based Lewis-acid catalyst framework.

17. The process of claim 1, wherein the solid silica-based Lewis-acid catalyst comprises M-BEA, where M is Sn, Ti, Zr, or a combination thereof, the ratio of Si to M is in a range of from about 50:1 to about 250:1.

18. The process of claim 9, wherein the molecular sieve comprises Sn-BEA, Ti-BEA, Zr-BEA, or a combination thereof.

19. The process of claim 1, wherein the solid silica-based Lewis-acid catalyst comprises amorphous silica.

20. The process of claim 1, wherein the solid silica-based Lewis-acid catalyst comprises mesoporous silica.

21. The process of claim 1, wherein the compound of Formula (3) is isolated.

22. The process of claim 1, wherein the compound of Formula (4) is isolated.

23. The process of claim 1, wherein the compound of Formula (3) is formed without the detectable presence of a corresponding compound of Formula (4).

24. The process of claim 1, wherein the compound of Formula (4) is formed without the detectable presence of a corresponding compound of Formula (3).

25. The process of claim 1, wherein the compound of Formula (4) is formed by the in situ dehydration of a corresponding compound of Formula (3).

26. The process of claim 1, wherein the non-aqueous solvent comprises 2-methyl-tetrahydrofuran, tetrahydrofuran, 1,4-dioxane, or γ-valerolactone.

27. The process of claim 26, wherein the non-aqueous solvent comprises 1,4-dioxane.

28. The process of claim 1, wherein contacting the compound of Formula (1) and Formula (2) in the presence of the solid, silica-based Lewis-acid catalyst is done at a temperature in a range of from about 50° C. to about 300° C.

29. The process of claim 1, wherein contacting the compound of Formula (1) and ethylene in the presence of the solid silica-based Lewis-acid catalyst is done at a total pressure in a range of from about 500 psig to about 1500 psig.

30. The process of claim 1, wherein the solid silica-based Lewis-acid catalyst is operated under reaction conditions sufficient to convert the compound of Formula (1) to the corresponding compound of Formula (3) or Formula (4) at a temperature in a range of from about 145° C. to about 250° C. with (a) a product yield of at least about 10%; or (b) a selectivity of at least 30%; or (c) both (a) and (b).

31. The process of claim 1, wherein the solid silica-based Lewis-acid catalyst is operated under reaction conditions sufficient to convert methyl 5-(methoxymethyl)furan-2-carboxylate (MMFC) to methyl 4-(methoxymethyl)benzenecarboxylate (MMBC) at temperatures in a range of from about 145° C. to about 250° C. with (a) a product yield of at least about 10%; or (b) a selectivity of at least 30%; or (c) both (a) and (b).

32. The process of claim 1, wherein the solid silica-based Lewis-acid catalyst is operated under reaction conditions sufficient to convert 5-(hydroxymethyl)furoic acid (HMFA) to 4-(hydroxymethyl)benzoic acid (HMBA) at temperatures in a range of from about 145° C. to about 250° C. with (a) a product yield of at least about 10%; (b) a selectivity of at least 30%; or (c) both (a) and (b).

33. The process of claim 1, comprising oxidizing or converting 4-hydroxymethyl furfural (HMF), formed by the dehydration of fructose, to a compound of claim 4, before contacting with the compound of Formula (2).

34. The process of claim 1, comprising oxidizing or converting 4-hydroxymethyl furfural (HMF) derived from biomass, to a compound of claim 4, before contacting with the compound of Formula (2).

35. The process of claim 28, wherein the temperature range is from about 150° C. to about 220° C.

* * * * *